US007709626B2

(12) United States Patent
Narayanan et al.

(10) Patent No.: US 7,709,626 B2
(45) Date of Patent: May 4, 2010

(54) PRIMER FOR NUCLEIC ACID DETECTION

(75) Inventors: Jothikumar Narayanan, Lawrenceville, GA (US); Vincent Hill, Decatur, GA (US)

(73) Assignee: The Government of the United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 12/267,869

(22) Filed: Nov. 10, 2008

(65) Prior Publication Data

US 2009/0118490 A1    May 7, 2009

Related U.S. Application Data

(63) Continuation of application No. 11/325,270, filed on Jan. 3, 2006, now abandoned.

(60) Provisional application No. 60/641,303, filed on Jan. 3, 2005.

(51) Int. Cl.
*C07H 21/04* (2006.01)
*C12Q 1/68* (2006.01)
*C12P 19/34* (2006.01)

(52) U.S. Cl. .......................... 536/24.3; 435/6; 435/91.2

(58) Field of Classification Search ....................... None
See application file for complete search history.

(56) References Cited

U.S. PATENT DOCUMENTS

| | | | |
|---|---|---|---|
| 5,563,253 | A | 10/1996 | Agrawal et al. |
| 5,827,657 | A | 10/1998 | Herrnstadt et al. |
| 6,028,190 | A | 2/2000 | Mathies et al. |
| 6,117,635 | A | 9/2000 | Nazarenko et al. |
| 6,472,153 | B1 | 10/2002 | Dempcy et al. |
| 6,492,121 | B2 | 12/2002 | Kurane et al. |
| 6,495,326 | B2 | 12/2002 | Kurane et al. |
| 6,635,427 | B2 | 10/2003 | Wittwer et al. |
| 6,699,661 | B1 | 3/2004 | Kurane et al. |
| 6,730,501 | B2 | 5/2004 | Eyre et al. |
| 2003/0022177 | A1 | 1/2003 | Wittwer et al. |
| 2003/0165859 | A1 | 9/2003 | Nazarenko et al. |
| 2003/0165867 | A1 | 9/2003 | Eyre et al. |
| 2004/0002098 | A1 | 1/2004 | Wittwer et al. |
| 2004/0067537 | A1 | 4/2004 | Hahn et al. |

OTHER PUBLICATIONS

Nazarenko et al. Effect of primary and secondary structure of oligodeoxyribonucleotides on the fluorescent properties of conjugated dyes. Nuc. Acids Res. 30(9):2089-2095 (2002).*
Marras et al. Efficiencies of fluorescence resonance energy transfer and contact-mediated quenching in oligonucleotide probes. Nuc. Acids Res. 30(21):e122 (pp. 1-8) (2002).*
Thelwell et al. Mode of action and application of Scorpion primers to mutation detection. Nucleic Acids Research 28(19):3752-61, 2000.*
Cairns et al., "Homogeneous Real-Time Detection and Quantification of Nucleic Acid Amplification Using Restriction Enzyme Digestion," *Biochem. Biophys. Res. Commun.* 318:684-690 (2004).
Castro et al., "Ultrasensitive Detection of DNA Sequences in Solution by Specific Enzymatic Labeling," *Anal. Chem.* 76:4169-4174 (2004).
Chen et al., "An Automated Fluorescent PCR Method for Detection of Shiga Toxin-Producing *Escherichia coli* in Foods," *Appl. Environ. Microbiol.* 64:4210-4116 (1998).
Crockett et al., "Fluorescein-Labeled Oligonucleotides for Real-Time PCR: Using the Inherent Quenching of Deoxyguanosine Nucleotides," *Analyt. Biochem.* 290:89-97 (2001).
Eragen Biosciences, http://www.eragen.com/diagnostics/genecode.html.
Fiandaca et al., "Self-Reporting PNA/DNA Primers for PCR Analysis," *Genome Res.* 11:609-613 (2001).
Guo and Milewicz, "Methodology for Using a Universal Primer to Label Amplified DNA Segments for Molecular Analysis," *Biotech. Lett.* 25:2079-2083 (2003).
Hirai et al., "Down-Regulation of Connexin 32 Gene Expression Through DNA Methylation in a Human Renal Cell Carcinoma Cell," *Am. J. Nephrol.* 23:172-177, 2003.
Kurata et al., "Fluorescent Quenching-Based Quantitative Detection of Specific DNA/RNA Using A BODIPY® FL-Labeled Probe or Primer," *Nucl. Acids Res.* 29:e34 (2001).
Lee et al., "Allelic Discrimination by Nick-Translation PCR with Fluorogenic Probes," *Nucleic Acids Res.* 21:3761-3766 (1993).
Li et al., "A New Class of Homogeneous Nucleic Acid Probes Based on Specific Displacement Hybridization," *Nucleic Acids Res.* 30:e5 (2002).
Marquez et al. "Selective Fluorescence Quenching of 2,3-Diazabicyclo[2.2.2]oct-2-ene by Nucleotides," *Org. Lett.* 5:3911-3914 (2003).
Nazarenko et al., "A Closed Tube Format for Amplification and Detection of DNA Based on Energy Transfer," *Nucleic Acids Res.* 25:2516-2521 (1997).
Nazarenko et al., "Multiplex Quantitative PCR Using Self-Quenched Primers Labeled with a Single Fluorophore," *Nucl. Acids Res.* 30:e37 (2002).
OG Notice: Examination of Patent Applications Containing Nucleotide Sequences, Feb. 22, 2007 (3 pages).
Ririe et al., "Product Differentiation by Analysis of DNA Melting Curves During the Polymerase Chain Reaction," *Anal. Biochem.* 245:154-160 (1997).
Ronaghi, "Pyrosequencing Sheds Light on DNA Sequencing," *Genome Res.* 11:3-11 (2001).

(Continued)

*Primary Examiner*—Young J Kim
*Assistant Examiner*—Samuel C Woolwine
(74) *Attorney, Agent, or Firm*—Klarquist Sparkman, LLP

(57) ABSTRACT

This application provides universal labeled primers for detection and amplification of nucleic acid molecules. These universal primers can be attached to the 5'-end of a target sequence-specific primer. In particular examples, the universal primer includes a labeled nucleotide flanked on both sides a nucleotide whose complement nucleotides changes a detectable signal from the label when the universal primer hybridizes with its complementary nucleic acid molecule. Also disclosed are methods of using the universal primer in nucleic acid amplification, such as real-time PCR.

25 Claims, 11 Drawing Sheets

OTHER PUBLICATIONS

Stratagene Catalog, 1988 (cover and p. 39).
Taguchi et al., "Age-Associated Changes in the Template-Reading Fidelity of DNA Polymerase α from Regenerating Rat Liver," *Mech. Ageing Dev.* 92:143-157, 1996.
Todd et al., "DzyNA-PCR: Use of DNAzymes to Detect and Quantify Nucleic Acid Sequences in a Real-Time Fluorescent Format," *Clin. Chem.* 46:625-630 (2000).
Torimura et al., "Fluorescence-Quenching Phenomenon by Photoinduced Electron Transfer between a Fluorescent Dye and a Nucleotide Base," *Anal Sci.* 17:155-160 (2001).
Tyagi and Kramer, "Molecular Beacons: Probes that Fluoresce upon Hybridization," *Nat. Biotechnol.* 14:303-308 (1996).
Whitcombe et al., "Detection of PCR Products Using Self-Probing Amplicons and Fluorescence," *Nat. Biotechnol.* 17:804-807 (1999).
Wittwer et al., "Continuous Fluorescence Monitoring of Rapid Cycle DNA Amplification," *Biotechniques* 22:130-138 (1997).
Wittwer et al., "High-Resolution Genotyping by Amplicon Melting Analysis Using LCGreen," *Clin. Chem.* 49:853-860 (2003).
Yamane et al., "MagiProbe: A Novel Fluorescence Quenching-Based Oligonucleotide Probe Carrying a Fluorophore and an Intercalator," *Nucl. Acids Res.* 30:e97 (2002).
Yguerabide et al., "Pyrene-Labeled DNA Probes for Homogeneous Detection of Complementary DNA Sequences: Poly(C) Model Systems," *Anal. Biochem.* 241:238-247, 1996.

* cited by examiner

FIG. 1 A

F*
5'-C*T*CCGGCxxxxxxxxxxx-3'

Carboxyfluorscein (F*)

FIG. 1 B

Forward primer with Tag

5'-CTCCGGCggagcctggagtacctgag————————————3'
3'-gaggccg————————————TTGTTCAAGTCTTGGGGTGTCA-5'
                                           Reverse primer

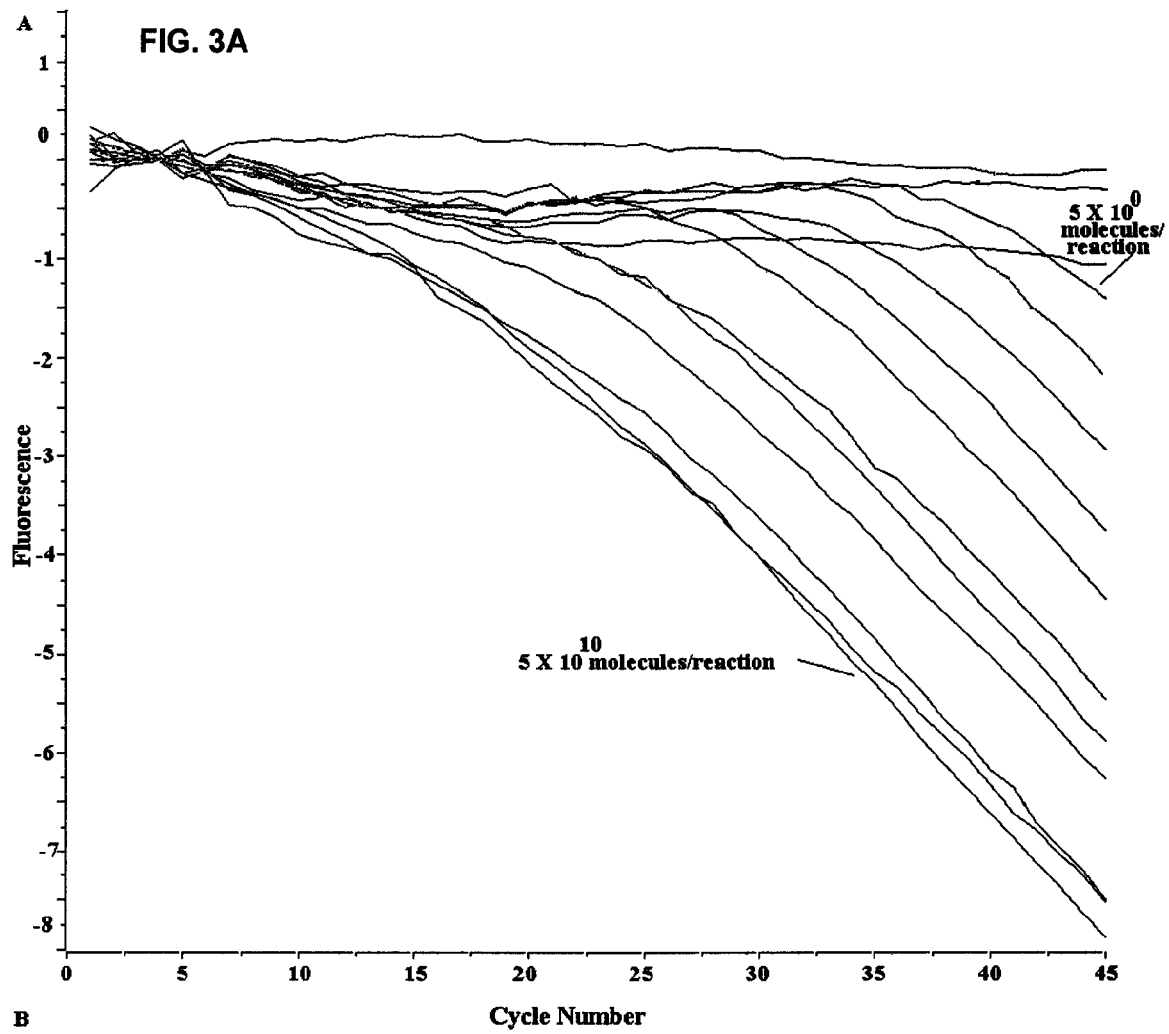
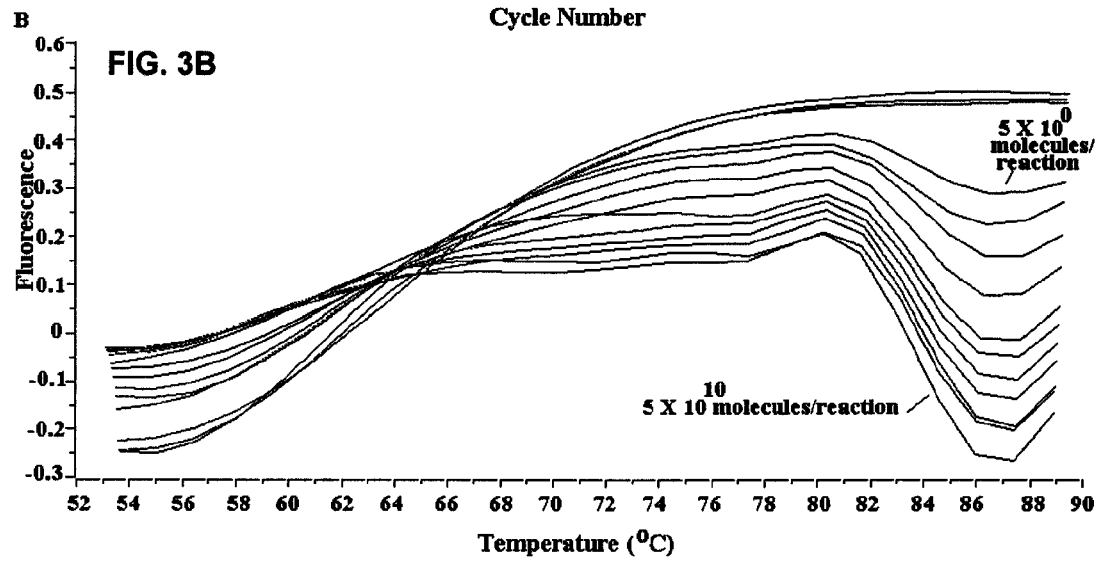

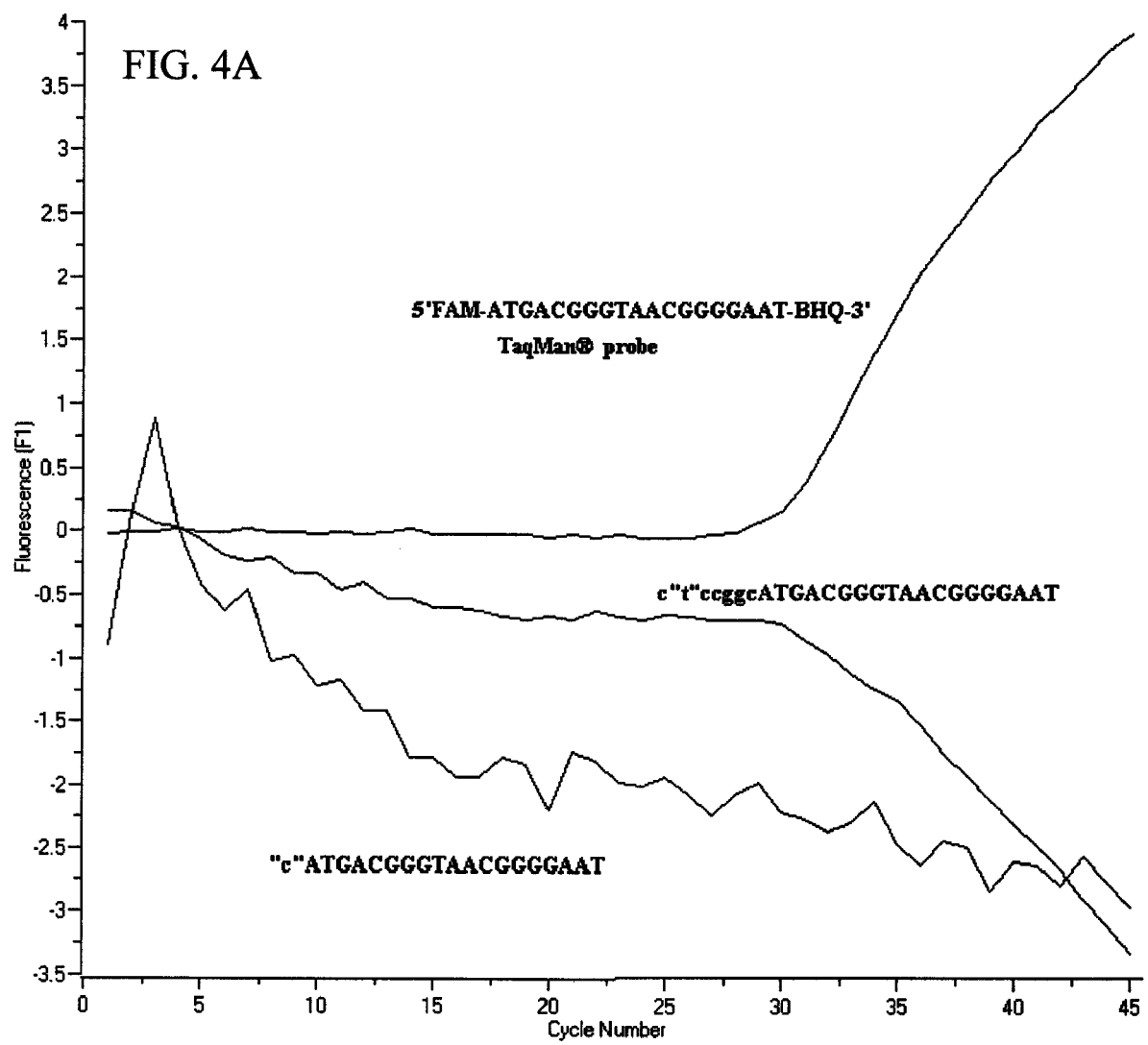
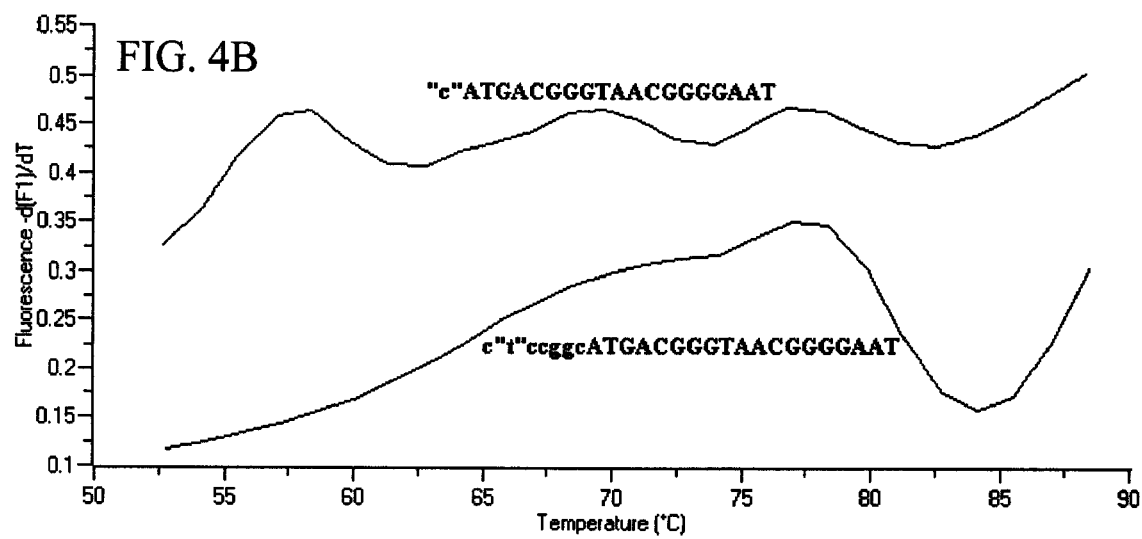

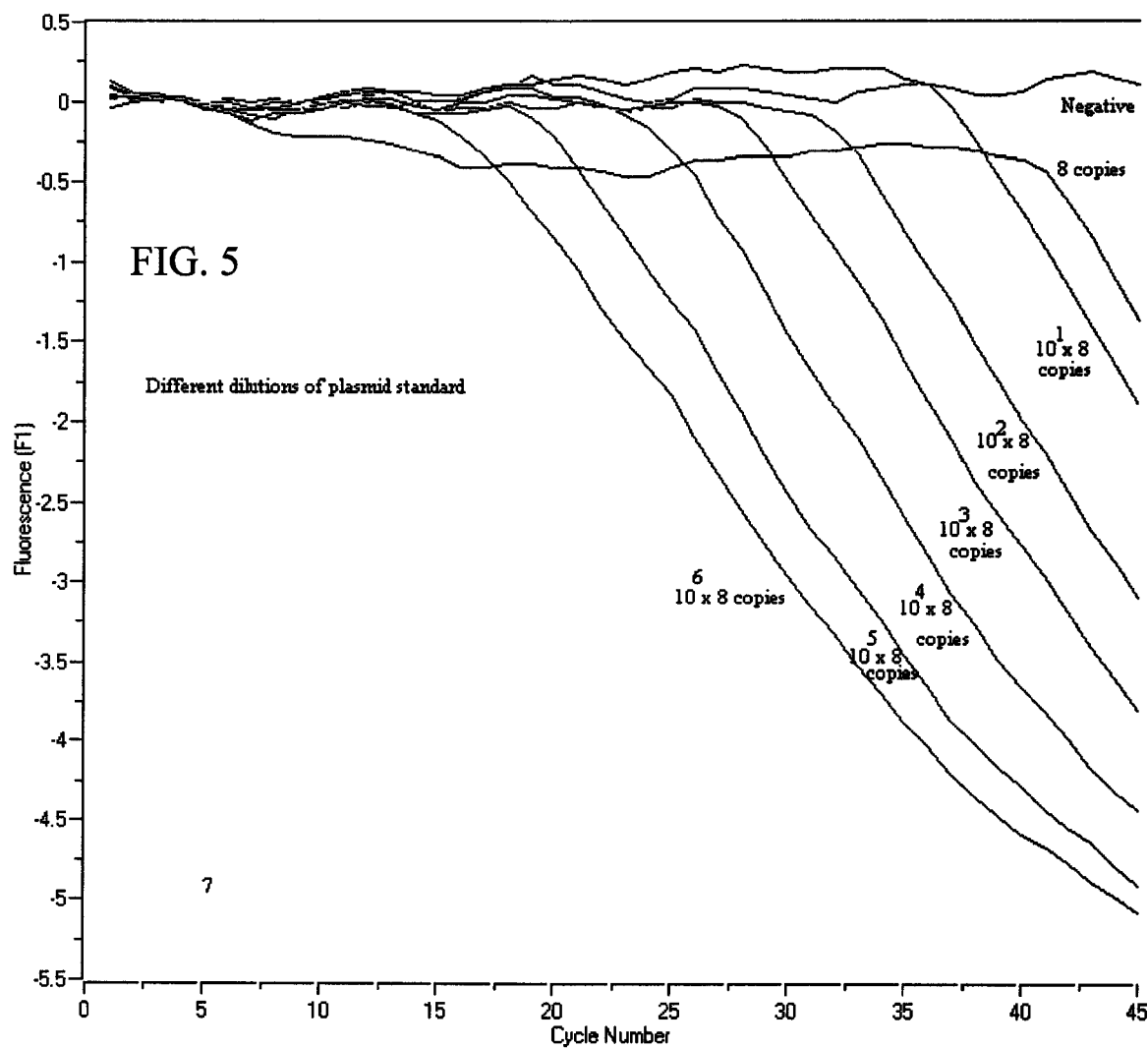

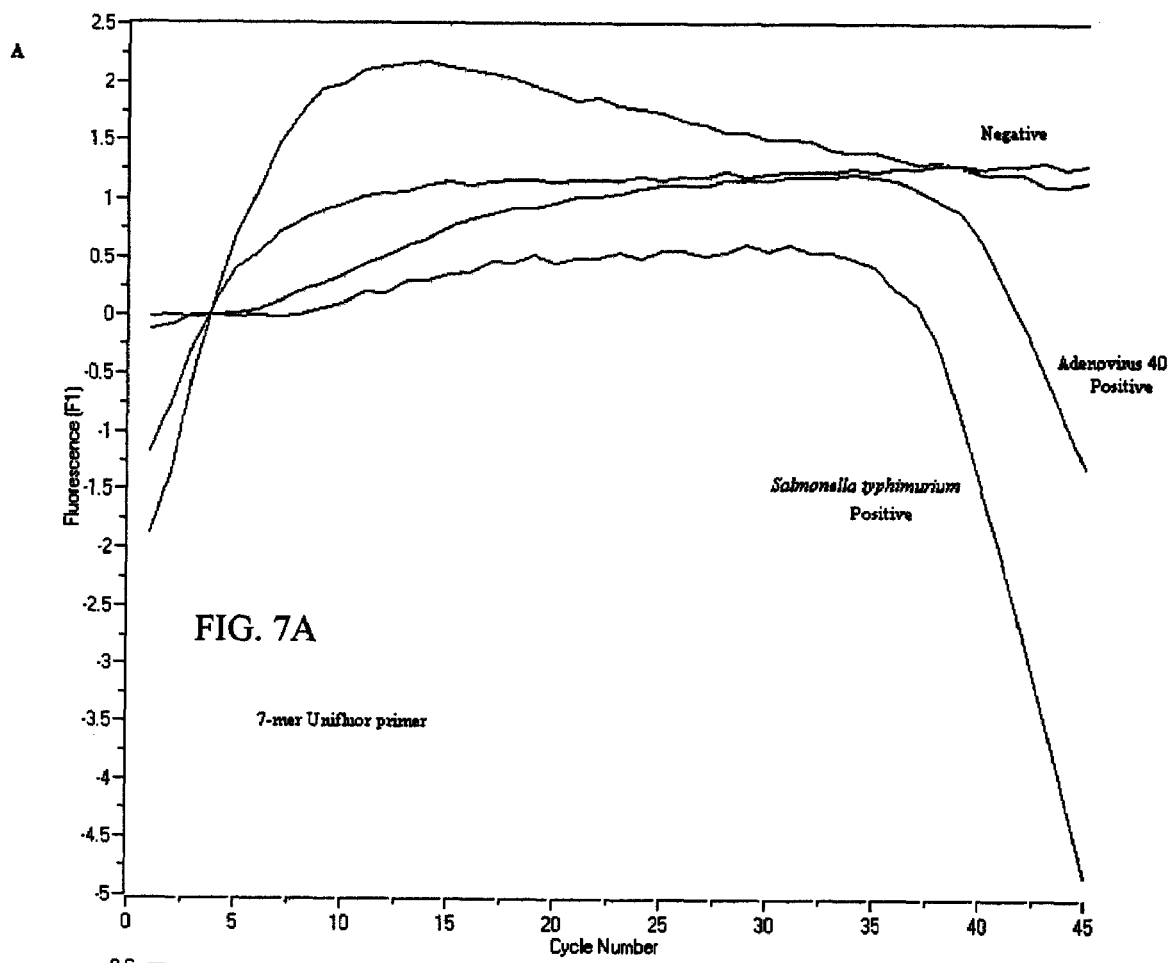
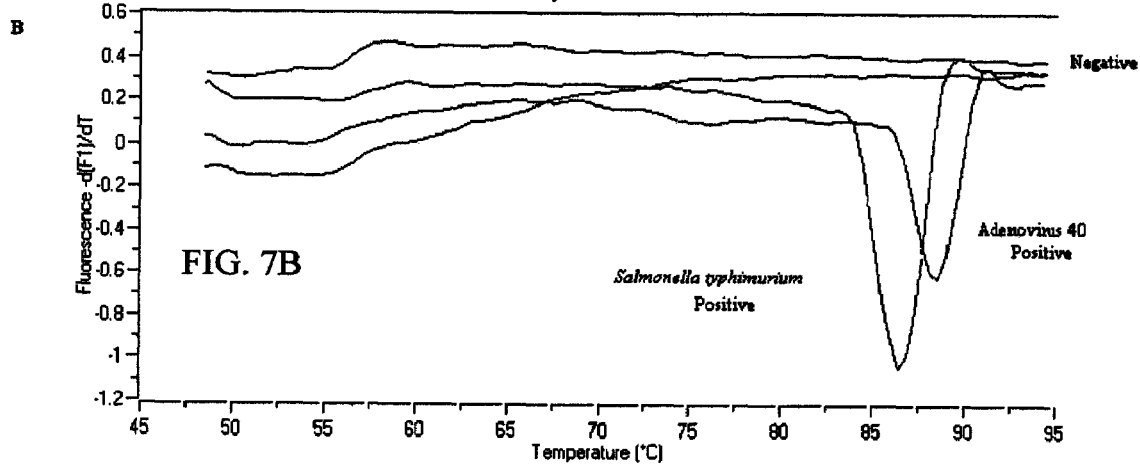
FIG. 7A
FIG. 7B

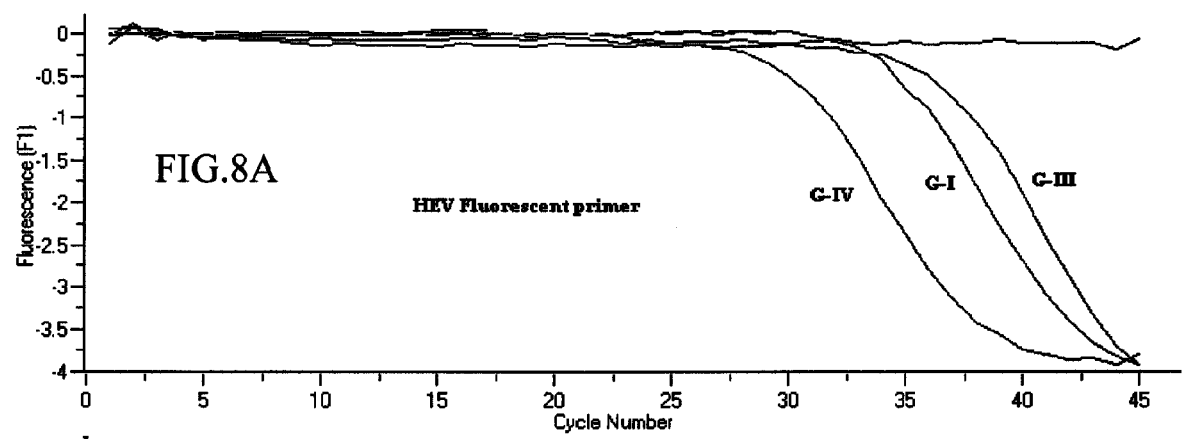
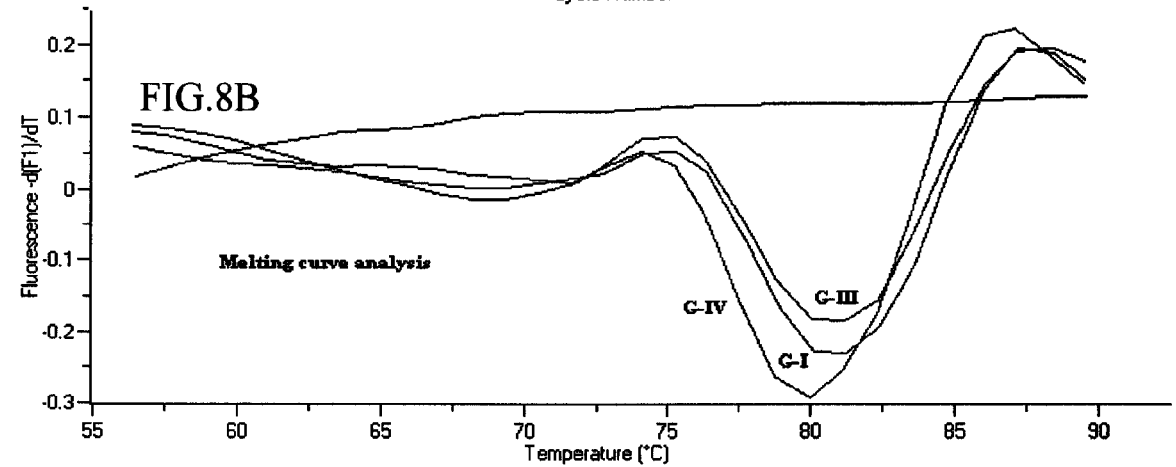

FIG. 10A
Light up Primer

```
       F      Probe region (Reverse)                            (Forward Primer)
5' ctccgcccGCGCCCGTCCTGCTGCCTTCCTTAGATGggcggag(X) ATGACGGGTAACGGGGAAT-3'
```

FIG. 10B

```
                       F
CGTCGTCCGCGcccgcctc-5'
::::::::
CTTCCTTAGATgggcggag(X) ATGACGGGTAACGGGGAAT-3' dG: -15.80 kcal/mol
     ⟶
```

FIG. 10C

```
                       F
CGTCGTCCGCGcccgcctc-5'                      (Forward Primer)
::::::::
CTTCCTTAGATgggcggag(X) ATGACGGGTAACGGGGAAT-3'
                     TACTGCCCATTGCCCCTTAatcccaagctaaggcctctccctcgactctttgccgatggtGTAGA-
TTCCTTCCGTCGTCCGCGCgttta...... Negative strand
     ⟶
```

FIG. 10D

```
   (Forward Primer)              Probe Region                                    F
tTAAGGGGCAATGGGCAGTA(X)gaggcgg                            ccgcctc-5'
                               GTAGATTCCTTCCGTCGTCCGCGGC
a                              CATCTAAGGAGGCAGCAGGGCGCGcaaattaccaatcctaatacagggaggtagtgacaagaaataacaatacCGACTTTTTGTTTTGTAATTGG
gggttcgattcggaggagaggagcctgagaaacggctaccaCATCTAAGGAGGCAGCAGGGCGCGcaaattaccaatcctaatacagggaggtagtgacaagaaataacaatacCGACTTTTTGTTTTGTAATTGG
(Positive strand)                                                                                              3'CCAATTACAAAACCAAAAAGTCC-5'
                                                                                                                (Reverse Primer)
```

F- Carboxyfluorescein
X- 3 carbon spacer

SEQUENCE LISTING

<160> NUMBER OF SEQ ID NOS: 34

<210> SEQ ID NO 1
<211> LENGTH: 7
<212> TYPE: DNA
<213> ORGANISM: Artificial
<220> FEATURE:
<223> OTHER INFORMATION: Exemplary universal primer
<220> FEATURE:
<221> NAME/KEY: misc_feature
<222> LOCATION: (2)..(2)
<223> OTHER INFORMATION: T at position 2 includes a detectable label.

<400> SEQUENCE: 1 ctccggc                                                                  7

<210> SEQ ID NO 2
<211> LENGTH: 28
<212> TYPE: DNA
<213> ORGANISM: Artificial
<220> FEATURE:
<223> OTHER INFORMATION: Forward primer for amplification of hexon
      protein of adenovirus.
<220> FEATURE:
<221> NAME/KEY: misc_feature
<222> LOCATION: (2)..(2)
<223> OTHER INFORMATION: T at position 2 includes a detectable label.

<400> SEQUENCE: 2
ctccggcgga cgcctcggag tacctgag                                           28

<210> SEQ ID NO 3
<211> LENGTH: 23
<212> TYPE: DNA
<213> ORGANISM: Artificial
<220> FEATURE:
<223> OTHER INFORMATION: Reverse primer for amplifying hexon protein
      region of adenovirus.
<220> FEATURE:
<221> NAME/KEY: misc_feature
<222> LOCATION: (3)..(3)
<223> OTHER INFORMATION: N at position 3 is inosine

<400> SEQUENCE: 3
acngtggggt ttctgaactt gtt                                                23

<210> SEQ ID NO 4
<211> LENGTH: 18
<212> TYPE: DNA
<213> ORGANISM: Artificial
<220> FEATURE:
<223> OTHER INFORMATION: Forward primer for TaqMan amplificaiton of the
      hexon protein region of adenovirus.

<400> SEQUENCE: 4

-continued tggccacccc ctcgatga                                           18

<210> SEQ ID NO 5
<211> LENGTH: 21
<212> TYPE: DNA
<213> ORGANISM: Artificial
<220> FEATURE:
<223> OTHER INFORMATION: Reverse primer for TaqMan amplificaiton of the
      hexon protein region of adenovirus.

<400> SEQUENCE: 5
tttgggggcc agggagttgt a                                       21

<210> SEQ ID NO 6
<211> LENGTH: 14
<212> TYPE: DNA
<213> ORGANISM: Artificial
<220> FEATURE:
<223> OTHER INFORMATION: Exemplary universal primer
<220> FEATURE:
<221> NAME/KEY: misc_feature
<222> LOCATION: (2)..(2)
<223> OTHER INFORMATION: T at position 2 includes a detectable label.

<400> SEQUENCE: 6
ctcggcccgc cgag                                               14

<210> SEQ ID NO 7
<211> LENGTH: 5
<212> TYPE: DNA
<213> ORGANISM: Artificial
<220> FEATURE:
<223> OTHER INFORMATION: Exemplary universal primer
<220> FEATURE:
<221> NAME/KEY: misc_feature
<222> LOCATION: (2)..(2)
<223> OTHER INFORMATION: T at position 2 includes a detectable label.
<220> FEATURE:
<221> NAME/KEY: misc_feature
<222> LOCATION: (5)..(5)
<223> OTHER INFORMATION: N at position 5 includes 0-11 nucleotides in
      any combination.

<400> SEQUENCE: 7 ctccn                                                         5

<210> SEQ ID NO 8
<211> LENGTH: 34
<212> TYPE: DNA
<213> ORGANISM: Artificial
<220> FEATURE:
<223> OTHER INFORMATION: Forward primer for amplication of a C. parvum
      sequence.
<220> FEATURE:
<221> NAME/KEY: misc_feature
<222> LOCATION: (2)..(2)
<223> OTHER INFORMATION: T at position 2 includes a detectable label.

<400> SEQUENCE: 8
ctccggcccg ccgagatgac gggtaacggg gaat                         34

<210> SEQ ID NO 9
<211> LENGTH: 30
<212> TYPE: DNA
<213> ORGANISM: Artificial
<220> FEATURE:
<223> OTHER INFORMATION: Forward primer for amplification of a C. parvum
      sequence.
<220> FEATURE:
<221> NAME/KEY: misc_feature

```
<222> LOCATION: (2)..(2)
<223> OTHER INFORMATION: T at position 2 includes a detectable label.

<400> SEQUENCE: 9
ctccggcccg catgacgggt aacggggaat                                    30

<210> SEQ ID NO 10
<211> LENGTH: 26
<212> TYPE: DNA
<213> ORGANISM: Artificial
<220> FEATURE:
<223> OTHER INFORMATION: Exemplary forward primer for amplification of a
      C. parvum sequence.
<220> FEATURE:
<221> NAME/KEY: misc_feature
<222> LOCATION: (2)..(2)
<223> OTHER INFORMATION: T at position 2 includes a detectable label.

<400> SEQUENCE: 10
ctccggcatg acgggtaacg gggaat                                        26

<210> SEQ ID NO 11
<211> LENGTH: 24
<212> TYPE: DNA
<213> ORGANISM: Artificial
<220> FEATURE:
<223> OTHER INFORMATION: Forward primer for amplification of a C. parvum
      sequence.
<220> FEATURE:
<221> NAME/KEY: misc_feature
<222> LOCATION: (2)..(2)
<223> OTHER INFORMATION: T at position 2 includes a detectable label.

<400> SEQUENCE: 11
ctccgatgac gggtaacggg gaat                                          24

<210> SEQ ID NO 12
<211> LENGTH: 23
<212> TYPE: DNA
<213> ORGANISM: Artificial
<220> FEATURE:
<223> OTHER INFORMATION: Forward primer for amplification of a C. parvum
      sequence.
<220> FEATURE:
<221> NAME/KEY: misc_feature
<222> LOCATION: (2)..(2)
<223> OTHER INFORMATION: T at position 2 includes a detectable label.

<400> SEQUENCE: 12
ctccatgacg ggtaacgggg aat                                           23

<210> SEQ ID NO 13
<211> LENGTH: 23
<212> TYPE: DNA
<213> ORGANISM: Artificial
<220> FEATURE:
<223> OTHER INFORMATION: Reverse primer for amplification of a C. parvum
      sequence.

<400> SEQUENCE: 13
ccaattacaa aaccaaaaag tcc                                           23

<210> SEQ ID NO 14
<211> LENGTH: 7
<212> TYPE: DNA
<213> ORGANISM: Artificial
<220> FEATURE:
<223> OTHER INFORMATION: Exemplary universal sequence.
<220> FEATURE:
```

```
<221> NAME/KEY: misc_feature
<222> LOCATION: (2)..(2)
<223> OTHER INFORMATION: T at position 2 includes a detectable label.

<400> SEQUENCE: 14 ctccggc                                                                    7

<210> SEQ ID NO 15
<211> LENGTH: 28
<212> TYPE: DNA
<213> ORGANISM: Artificial
<220> FEATURE:
<223> OTHER INFORMATION: Forward primer for amplification of the hexon
      protein region of Adenovirus.
<220> FEATURE:
<221> NAME/KEY: misc_feature
<222> LOCATION: (2)..(2)
<223> OTHER INFORMATION: T at position 2 includes a detectable label.

<400> SEQUENCE: 15
ctccggcgga cgcctcggag tacctgag                                            28

<210> SEQ ID NO 16
<211> LENGTH: 27
<212> TYPE: DNA
<213> ORGANISM: Artificial
<220> FEATURE:
<223> OTHER INFORMATION: Forward primer for amplification of a S.
      typhimurium sequence.
<220> FEATURE:
<221> NAME/KEY: misc_feature
<222> LOCATION: (2)..(2)
<223> OTHER INFORMATION: T at position 2 includes a detectable label.

<400> SEQUENCE: 16
ctccggcgcc tttctccatc gtcctga                                             27

<210> SEQ ID NO 17
<211> LENGTH: 19
<212> TYPE: DNA
<213> ORGANISM: Artificial
<220> FEATURE:
<223> OTHER INFORMATION: Reverse primer for amplification of a S.
      typhimurium sequence.

<400> SEQUENCE: 17
tggtgttatc tgcctgacc                                                      19

<210> SEQ ID NO 18
<211> LENGTH: 5
<212> TYPE: DNA
<213> ORGANISM: Artificial
<220> FEATURE:
<223> OTHER INFORMATION: Exemplary universal primer
<220> FEATURE:
<221> NAME/KEY: misc_feature
<222> LOCATION: (2)..(2)
<223> OTHER INFORMATION: T at position 2 includes a detectable label.
<220> FEATURE:
<221> NAME/KEY: misc_feature
<222> LOCATION: (5)..(5)
<223> OTHER INFORMATION: N at position 5 is zero or any number of
      nucleotides in any order.

<400> SEQUENCE: 18 ctccn                                                                      5

<210> SEQ ID NO 19
<211> LENGTH: 5
```

```
<212> TYPE: DNA
<213> ORGANISM: Artificial
<220> FEATURE:
<223> OTHER INFORMATION: Exemplary universal primer.
<220> FEATURE:
<221> NAME/KEY: misc_feature
<222> LOCATION: (2)..(2)
<223> OTHER INFORMATION: T at position 2 includes a detectable label.
<220> FEATURE:
<221> NAME/KEY: misc_feature
<222> LOCATION: (5)..(5)
<223> OTHER INFORMATION: N at position 5 includes zero or any number of
      nucleotides in any order.

<400> SEQUENCE: 19 ctcgn                                                                   5

<210> SEQ ID NO 20
<211> LENGTH: 5
<212> TYPE: DNA
<213> ORGANISM: Artificial
<220> FEATURE:
<223> OTHER INFORMATION: Exemplary universal primer.
<220> FEATURE:
<221> NAME/KEY: misc_feature
<222> LOCATION: (2)..(2)
<223> OTHER INFORMATION: T at position 2 includes a detectable label.
<220> FEATURE:
<221> NAME/KEY: misc_feature
<222> LOCATION: (4)..(4)
<223> OTHER INFORMATION: S at position 4 is G or C.
<220> FEATURE:
<221> NAME/KEY: misc_feature
<222> LOCATION: (5)..(5)
<223> OTHER INFORMATION: n at position 5 includes nay number of
      nucleotides in any order.

<400> SEQUENCE: 20 ctcsn                                                                   5

<210> SEQ ID NO 21
<211> LENGTH: 7
<212> TYPE: DNA
<213> ORGANISM: Artificial
<220> FEATURE:
<223> OTHER INFORMATION: T at position 2 includes a detectable label; X
      is any nucleotide; and S is a G or a C.
<220> FEATURE:
<221> NAME/KEY: misc_feature
<222> LOCATION: (2)..(2)
<223> OTHER INFORMATION: T at position 2 includes a detectable label.
<220> FEATURE:
<221> NAME/KEY: misc_feature
<222> LOCATION: (4)..(4)
<223> OTHER INFORMATION: S at position 4 is C or G.
<220> FEATURE:
<221> NAME/KEY: misc_feature
<222> LOCATION: (5)..(6)
<223> OTHER INFORMATION: N is any nucleotide.
<220> FEATURE:
<221> NAME/KEY: misc_feature
<222> LOCATION: (7)..(7)
<223> OTHER INFORMATION: n is a, c, g, or t

<400> SEQUENCE: 21 ctcsnnn                                                                 7

<210> SEQ ID NO 22
<211> LENGTH: 7
<212> TYPE: DNA
<213> ORGANISM: Artificial
<220> FEATURE:
<223> OTHER INFORMATION: Exemplary universal primer.
```

```
<220> FEATURE:
<221> NAME/KEY: misc_feature
<222> LOCATION: (2)..(2)
<223> OTHER INFORMATION: T at position 2 includes a detectable label.
<220> FEATURE:
<221> NAME/KEY: misc_feature
<222> LOCATION: (4)..(4)
<223> OTHER INFORMATION: S at position 4 is G or C.
<220> FEATURE:
<221> NAME/KEY: misc_feature
<222> LOCATION: (5)..(6)
<223> OTHER INFORMATION: n at positions 5-6 is any nucleotide.
<220> FEATURE:
<221> NAME/KEY: misc_feature
<222> LOCATION: (7)..(7)
<223> OTHER INFORMATION: n at position 7 is zero or any number of
      nucleotides in any order.

<400> SEQUENCE: 22 ctcsnnn                                                                    7

<210> SEQ ID NO 23
<211> LENGTH: 7
<212> TYPE: DNA
<213> ORGANISM: Artificial
<220> FEATURE:
<223> OTHER INFORMATION: Complementary sequence to the universal primer
      of SEQ ID NO: 1.

<400> SEQUENCE: 23 gaggccg                                                                    7

<210> SEQ ID NO 24
<211> LENGTH: 20
<212> TYPE: DNA
<213> ORGANISM: Artificial
<220> FEATURE:
<223> OTHER INFORMATION: Forward primer for amplification of 18s region
      of C. parvum.
<220> FEATURE:
<221> NAME/KEY: misc_feature
<222> LOCATION: (1)..(1)
<223> OTHER INFORMATION: C includes a detectable label.

<400> SEQUENCE: 24
catgacgggt aacggggaat                                                     20

<210> SEQ ID NO 25
<211> LENGTH: 19
<212> TYPE: DNA
<213> ORGANISM: Artificial
<220> FEATURE:
<223> OTHER INFORMATION: TaqMan probe for amplification of 18s region of
      C. parvum.
<220> FEATURE:
<221> NAME/KEY: misc_feature
<222> LOCATION: (1)..(19)
<223> OTHER INFORMATION: 5' end includes FAM and 3' end includes BHQ

<400> SEQUENCE: 25
atgacgggta acggggaat                                                      19

<210> SEQ ID NO 26
<211> LENGTH: 25
<212> TYPE: DNA
<213> ORGANISM: Artificial
<220> FEATURE:
<223> OTHER INFORMATION: Forward primer for amplification of Hepatitis
      E.
<220> FEATURE:
<221> NAME/KEY: misc_feature
```

```
<222> LOCATION: (2)..(2)
<223> OTHER INFORMATION: T is labeled with a detectable label such as
      6-carboxy fluorescein

<400> SEQUENCE: 26
ctccggcggt ggtttctggg gtgac                                           25

<210> SEQ ID NO 27
<211> LENGTH: 18
<212> TYPE: DNA
<213> ORGANISM: Artificial
<220> FEATURE:
<223> OTHER INFORMATION: Reverse primer for amplification of Hepatitis
      E.

<400> SEQUENCE: 27
aggggttggt tggatgaa                                                   18

<210> SEQ ID NO 28
<211> LENGTH: 7
<212> TYPE: DNA
<213> ORGANISM: Artificial
<220> FEATURE:
<223> OTHER INFORMATION: Exemplary universal primer.
<220> FEATURE:
<221> NAME/KEY: misc_feature
<222> LOCATION: (2)..(2)
<223> OTHER INFORMATION: T at position 2 includes a detectable label.

<400> SEQUENCE: 28 ctccata                                                                7

<210> SEQ ID NO 29
<211> LENGTH: 58
<212> TYPE: DNA
<213> ORGANISM: Artificial
<220> FEATURE:
<223> OTHER INFORMATION: Primer for amplification of the 18s region of
      C. parvum.
<220> FEATURE:
<221> NAME/KEY: misc_feature
<222> LOCATION: (2)..(2)
<223> OTHER INFORMATION: T at position 2 includes a detectable lable
      such as 6-carboxy fluorescein
<220> FEATURE:
<221> NAME/KEY: misc_feature
<222> LOCATION: (39)..(39)
<223> OTHER INFORMATION: N at position 39 is a C3 spacer amidite

<400> SEQUENCE: 29
ctccgcccgc gcctgctgcc ttccttagat gggcggagna tgacgggtaa cggggaat      58

<210> SEQ ID NO 30
<211> LENGTH: 8
<212> TYPE: DNA
<213> ORGANISM: Artificial
<220> FEATURE:
<223> OTHER INFORMATION: Complementary to nucleotides 1-8 of SEQ ID NO:
      29.

<400> SEQUENCE: 30 gaggcggg                                                               8

<210> SEQ ID NO 31
<211> LENGTH: 15
<212> TYPE: DNA
<213> ORGANISM: Artificial
<220> FEATURE:
<223> OTHER INFORMATION: Exemplary universal primer
```

```
<220> FEATURE:
<221> NAME/KEY: misc_feature
<222> LOCATION: (2)..(2)
<223> OTHER INFORMATION: T includes a detectable label
<220> FEATURE:
<221> NAME/KEY: misc_feature
<222> LOCATION: (4)..(7)
<223> OTHER INFORMATION: S is G or C
<220> FEATURE:
<221> NAME/KEY: misc_feature
<222> LOCATION: (8)..(8)
<223> OTHER INFORMATION: N is any number of nucleotides
<220> FEATURE:
<221> NAME/KEY: misc_feature
<222> LOCATION: (9)..(12)
<223> OTHER INFORMATION: R is the complementary nucleotide to S

<400> SEQUENCE: 31
ctcssssnrr rrgag                                                          15

<210> SEQ ID NO 32
<211> LENGTH: 17
<212> TYPE: DNA
<213> ORGANISM: Artificial
<220> FEATURE:
<223> OTHER INFORMATION: Exemplary universal primer
<220> FEATURE:
<221> NAME/KEY: misc_feature
<222> LOCATION: (2)..(2)
<223> OTHER INFORMATION: T includes a detectable label
<220> FEATURE:
<221> NAME/KEY: misc_feature
<222> LOCATION: (4)..(7)
<223> OTHER INFORMATION: S is G or C
<220> FEATURE:
<221> NAME/KEY: misc_feature
<222> LOCATION: (8)..(8)
<223> OTHER INFORMATION: N is any number of nucleotides
<220> FEATURE:
<221> NAME/KEY: misc_feature
<222> LOCATION: (9)..(12)
<223> OTHER INFORMATION: R is the complementary nucleotide to S
<220> FEATURE:
<221> NAME/KEY: misc_feature
<222> LOCATION: (13)..(13)
<223> OTHER INFORMATION: N is a carbon spacer arm of at least 3 carbons
<220> FEATURE:
<221> NAME/KEY: misc_feature
<222> LOCATION: (16)..(16)
<223> OTHER INFORMATION: N is a carbon spacer arm of at least 3 carbons
<220> FEATURE:
<221> NAME/KEY: misc_feature
<222> LOCATION: (17)..(17)
<223> OTHER INFORMATION: N is any number of nucleotides

<400> SEQUENCE: 32
ctcssssnrr rrgagnn                                                        17

<210> SEQ ID NO 33
<211> LENGTH: 90
<212> TYPE: DNA
<213> ORGANISM: Artificial
<220> FEATURE:
<223> OTHER INFORMATION: exemplary complementary sequence shown in FIG.
      10C

<400> SEQUENCE: 33
tactgcccat tgccccttaa tcccaagcta aggcctctcc ctcggactct ttgccgatgg          60
tgtagattcc ttccgtcgtc cgcgcgttta                                          90

<210> SEQ ID NO 34
<211> LENGTH: 137
```

-continued

```
<212> TYPE: DNA
<213> ORGANISM: Artificial
<220> FEATURE:
<223> OTHER INFORMATION: exemplary complementary sequence shown in FIG.
      10D

<400> SEQUENCE: 34
gggttcgatt ccggagaggg agcctgagaa acggctacca catctaagga aggcagcagg      60
cgcgcaaatt acccaatcct aatacaggga ggtagtgaca agaaataaca atacggactt    120
tttggttttg taattgg                                                   137
```

PRIMER FOR NUCLEIC ACID DETECTION

CROSS-REFERENCE TO RELATED APPLICATIONS

This is a continuation of U.S. patent application Ser. No. 11/325,270 filed Jan. 3, 2006, now abandoned which claims priority to U.S. Provisional Application No. 60/641,303 filed Jan. 3, 2005, both of which applications are herein incorporated by reference.

FIELD

The present disclosure relates to labeled nucleic acid sequences and methods of their use, for example to detect or amplify a nucleic acid molecule.

BACKGROUND

The real-time polymerase chain reaction (PCR) is currently used as a diagnostic tool in clinical applications. The real-time PCR assay is carried out in the closed-tube format and can be used to obtain quantitative results. The chemistry of real-time PCR is based on monitoring fluorescence at every cycle at a set temperature that facilitates calculating the kinetics of the product formed and performing melting curve analysis to identify formation of the specific product. Fluorescence is usually monitored using an optical device to collect the data at specific excitation and emission wavelengths for the particular fluorescent dye present in the sample.

One method used to monitor nucleic acid amplification is the addition of SYBR Green I dye (Ririe et al., *Anal. Biochem.* 245:154-60, 1997) and LCGreen (Wittwer et al., *Clin. Chem.* 49:853-60, 2003) during PCR. During amplification, these fluorophores are excited with the appropriate wavelength of light, inducing fluorescence when the dye intercalates into a DNA double helix. However, this method lacks specificity and the primer-dimer can also fluoresce.

Specificity can be increased by using a labeled sequence-specific probe. Several of such methods are currently available for performing real-time PCR, such as TaqMan® probes (Lee et al., *Nucleic Acids Res.* 21:3761-6, 1993); molecular beacons (Tyagi and Kramer, *Nat. Biotechnol.* 14:303-8, 1996); self-probing amplicons (scorpions) (Whitcombe et al., *Nat. Biotechnol.* 17:804-7, 1999); Amplisensor (Chen et al., *Appl. Environ. Microbiol.* 64:4210-6, 1998); Amplifluor (Nazarenko et al., *Nucleic Acids Res.* 25:2516-21, 1997 and U.S. Pat. No. 6,117,635); displacement hybridization probes (Li et al., *Nucleic Acids Res.* 30:E5, 2002); DzyNA-PCR (Todd et al., *Clin. Chem.* 46:625-30, 2000); fluorescent restriction enzyme detection (Cairns et al. *Biochem. Biophys. Res. Commun.* 318:684-90, 2004); and adjacent hybridization probes (Wittwer et al., *Biotechniques* 22:130-1, 134-8, 1997).

Currently available labeled primers can have a secondary structure that is complex and in some instances must be synthesized using specialized procedures. For example LUX™ primers (Invitrogen Corp.) are fluorescently labeled on the 3'-end and have a stem-loop structure that must be denatured for the primer to work efficiently (especially for reverse transcription). The design of the LUX™ primer is also a time-consuming step, which requires specific software.

Several publications disclose probes that contain only one fluorophore for use in detecting the presence of a particular nucleic acid (for example see U.S. Pat. No. 6,699,661; U.S. Pat. No. 6,495,326; and U.S. Pat. No. 6,492,121 (all to Kurane et al.); U.S. Pat. No. 6,635,427 (Wittwer et al.); Kurata et al. (*Nucl. Acids Res.* 29:e34, 2001); Torimura et al. (*Analyt. Sci.* 17:155-60, 2001); and Crockett et al. (*Analyt. Biochem.* 290:89-97, 2001)). In these examples, the fluorophore is present on the very end of the probe and the fluorescent signal is either enhanced or quenched in the presence of the target nucleic acid sequence, depending on the particular design of the probe. In most cases, the labeled primer specifically hybridizes to the target nucleic acid sequence. Guo and Milewicz (*Biotech. Lett.* 25:2079-83, 2003) disclose universal fluorescent tag primers labeled on the 5' end that are not sequence specific. The labeled fluorescent tag universal primer, in combination with two sequence-specific primers, are use to amplify a target nucleic acid sequence.

Yamane (*Nucl. Acids Res.* 30:e97, 2002) discloses a MagniProbe that has an internal fluorophore and an internal intercalator. The fluorescence is quenched by the intercalator in the absence of a target sequence. Upon hybridization with the target sequence, the probe emits fluorescence due to the interference in quenching by intercalation.

Nazarenko et al. (*Nucl. Acids Res.* 30:e37, 2002) disclose a probe with a single fluorophore near the 3' end (but no quencher), and addition of 5-7 base pairs to the 5' end of the sequence-specific probe, wherein the signal from the fluorophore is increased in the presence of the target sequence.

SUMMARY

The present application relates to novel universal sequences (also referred to herein as universal primers or tags) as well as their use, for example in assessing the progress of a PCR reaction, such as real time PCR, or for assessing the progress of melting duplex DNA, such as an amplicon. The novel universal tags include a label with a detectable signal that is altered by one or more nucleotides in its complement sequence when the universal tag hybridizes to its complement sequence.

The disclosed universal nucleic acid sequences include a 5'-end, a 3'-end, and a labeled nucleotide, wherein the labeled nucleotide is flanked by two nucleotides whose complement nucleotides change a detectable signal from the label when the universal tag hybridizes with its complementary sequence. For example, if the labeled nucleotide is "T", and the universal tag includes the sequence CTC, the C's are the two nucleotides that flank the labeled nucleotide, and a signal from the detectable label on the "T" changes when the CTC sequence hybridizes to its complementary sequence GAG.

In particular examples, a universal tag includes the sequence 5'-$X_{1(n)}X_2X_3X_4X_{5(n)}$-3', wherein $X_3$ is a labeled nucleotide that that emits a detectable signal, wherein $X_2$ and $X_4$ are the two flanking nucleotides that hybridize to complementary nucleotides that alter the detectable signal in a predictable manner, and n is zero, one, two or more nucleotides. In some examples, the nucleotide that includes the label is $X_2$ or $X_4$, wherein $X_1$ and $X_3$ or $X_3$ and $X_5$, respectively, are nucleotides that hybridize to nucleotides that alter the detectable signal in a predictable manner, and $X_4$ and $X_5$ or $X_1$ and $X_2$ are zero, one, two or more nucleotides, respectively.

In a specific example, a universal tag includes the sequence 5'-$X_2X_3X_4X_{5(n)}$-3', wherein $X_3$ is a nucleotide that includes a label that emits a detectable signal, wherein $X_2$ and $X_4$ are the flanking nucleotides that hybridize to complementary nucleotides that alter the detectable signal in a predictable manner, and $X_{5(n)}$ is one or more nucleotides (and $X_1$ which is not present in this example is zero nucleotides).

In specific examples, the nucleotide containing a label is "T". In some examples, the flanking nucleotides that hybridize to complementary nucleotides that alter the detectable signal are "C". For example, in the sequence 5'-$X_2X_3X_4$ $X_{5(n)}$-3', $X_3$ can be a "T" that includes a fluorophore whose signal is decreased upon hybridization to a complementary sequence, $X_2$ and $X_4$ are "C" that hybridize to "G" in a complementary sequence wherein "G" decreases fluorescence emitted from the fluorophore, and $X_5$ is a "C" (or any other nucleotide such as a "G") followed by at least one additional nucleotide, such as at least 2 nucleotides, at least 5 nucleotides, at least 10 nucleotides, or 1-50 nucleotides, such as 1-10 nucleotides. However, one skilled in the art will appreciate that the labeled nucleotide can be another nucleotide such as A, C, G, U, or a modified nucleotide such as inosine. Similarly, the nucleotides that hybridize to nucleotides that alter the detectable signal in a predictable manner can be other nucleotides, such as nucleotides that are capable of quenching a fluorescent-labeled nucleotide, for example the synthetic nucleotide isoC.

In particular examples, the label on the universal tag is present on a nucleotide that is the second nucleotide from the 5'-end. This position can also be referred to as the 0 position, and the flanking nucleotides referred to as the −1 and +1 positions. For example, the nucleotide that is two nucleotides from the 5' end (or the 0 position) of the universal sequence 5'-$X_1X_2X_3X_4X_5$-3' is $X_2$, and the flanking nucleotides $X_1$ and $X_3$ (or the −1 and +1 positions, respectively). Similarly, the nucleotide that is two nucleotides from the 5' end (or the 0 position) of the universal sequence 5'-CTCC$X_{(n)}$ (SEQ ID NO: 18) or 5'-CTCG$X_{(n)}$ (SEQ ID NO: 19) is the "T". Although particular exemplary universal primers are disclosed herein (for example SEQ ID NOS: 1, 6, 7, 14, and 18-22), the present application is not limited to these particular sequences.

The signal from the label changes when the universal nucleic acid sequence is hybridized to its complementary sequence. The change in the signal can be an increase or a decrease. The resulting change in detectable signal is proportional to the amount of amplicon produced and therefore occurs only when a complimentary stand is synthesized. The signal can be detected by a variety of devices, such as fluorescent microtiter plate readers, spectrofluorometers, fluorescent imaging systems, and real-time PCR instruments.

Any label whose signal is changed in response to hybridization to a nucleic acid molecule can be used, such as a fluorophore, for example 6-carboxyfluorescein (6-FAM). In particular examples, the change in signal is a decrease in fluorescence, such as a quenching of fluorescence. For example, the nucleotide guanosine can quench a variety of fluorophores, such as 6-FAM.

Ideally, a universal nucleic acid sequence does not recognize and hybridize to a target nucleic acid sequence. For example, if the target nucleic acid sequence is a human p53 sequence, the universal nucleic acid sequence does not substantially hybridize to the p53 sequence. In particular examples, the universal nucleic acid sequence alone does not hybridize with a target nucleic acid sequence under moderately stringent or highly stringent hybridization conditions.

The disclosed universal sequences can be used to label any sequence-specific primer without significantly affecting the sensitivity of the amplification reaction. Ideally, a sequence-specific primer specifically recognizes a target nucleic acid sequence. For example, if the target sequence is a human p53 sequence, the sequence specific primer can substantially hybridize to the p53 sequence. In some examples, a sequence specific primer can hybridize with a target nucleic acid sequence under moderately stringent or highly stringent hybridization conditions.

A universal tag can be attached via its 3'-end to a 5'-end of a forward primer or a reverse primer specific for the target nucleic acid sequence of interest, thereby generating a labeled forward or labeled reverse primer. The resulting labeled forward or labeled reverse primer can be used to amplify the appropriate target nucleic acid, for example using real-time PCR, resulting in the formation of amplicon products. The method can further include quantifying an amount of target nucleic acid sequence present in a sample.

Also provided by the present disclosure are kits that include one or more universal nucleic acid sequences of the present disclosure. The kits can further include a ligase to permit joining of the 3'-end of a universal nucleic acid tag to a 5'-end of a sequence-specific forward or reverse primer. In some examples, the kit also includes one or more sequence-specific forward or reverse primers, such as primers that recognize and can be used to amplify a target sequence of interest. In a specific example, the sequence-specific forward or reverse primer hybridizes specifically to a pathogen's nucleic acid sequence, such as a viral, bacterial, parasitic, or fungal nucleic acid sequence. In another specific example, the sequence-specific forward or reverse primer hybridizes specifically to a human nucleic acid sequence.

Arrays, such as a DNA microarray, that include one or more of the disclosed universal tags are encompassed by this disclosure. Such arrays can be used to determine whether a desired target sequence is present, such as in a sample. The disclosed universal tags can be hybridized to a target nucleic acid sequence attached to the array (for example resulting in fluorescence).

The disclosed universal tags provide an approach to detect, and in some examples further quantify, a target nucleic acid. Use of the universal tags is shown herein to provide a highly sensitive detection method, which permits detected of small quantities of target nucleic acid molecule, such as DNA. For example, the present disclosure provides methods of detecting a target nucleic acid molecule. The method includes incubating a sample containing nucleic acids (such as DNA or RNA) with a universal tag which is linked to a forward or a reverse target sequence specific primer, and with the corresponding forward or reverse target sequence specific primer not containing the universal tag. The sample and labeled forward primer and reverse primer not containing the universal tag, or forward primer not containing the universal tag and labeled reverse primers are incubated under conditions sufficient to permit amplification of the target nucleic acid. A change in signal from the label on the universal tag is monitored, wherein a change in signal indicates the presence of the target nucleic acid sequence. In particular examples, both the forward and reverse target sequence specific primers contain a universal tag.

In some examples, the change in signal is monitored during the amplification reaction, for example in real time as the amplicons are formed. In other or additional examples, the change in signal is monitored after the amplification, for example by exposing the resulting amplicons to increased temperature to generate a melting curve. Melting curve analysis can be used to confirm the presence of a target nucleic acid, and can also be used to distinguish polymorphisms in amplicons.

Those skilled in the art will appreciate that the disclosed nucleic acid molecules and methods can be used to amplify two or more different target nucleic acid molecules (such as at least 2, at least 3, at least 4, or even at least 5 different nucleic acid sequences) in the same amplification reaction. In particular examples, two or more different primers, each containing a different label, are used. In other examples, the same universal tag sequence and label are ligated to at least two different sequence-specific primers, wherein the resulting amplicons are differentiated, for example by using melting curve analysis. In yet other examples, combinations of the same universal tag sequence and label or different universal tag sequences and labels are used.

BRIEF SUMMARY OF THE DRAWINGS

FIGS. 1A and 1B are schematic drawings showing (A) an exemplary fluorescently labeled universal primer (SEQ ID NO: 1) and (B) a stable hybrid that results when the amplicon is formed in the region of the universal primer and the sequence-specific primer. Labeling position is shown with a letter F* and the Tag region is capitalized. Forward primer with universal primer is shown in SEQ ID NO: 2 and the reverse primer is shown in SEQ ID NO: 3.

FIG. 3A is a graph showing the fluorescence quenching of an exemplary universal primer (SEQ ID NO: 1) during PCR amplification of 10-fold dilutions of adenovirus 40 GE copies.

FIG. 3B is a graph showing the melting curve analysis of PCR amplicons generated from the assays shown in FIG. 3A.

FIG. 4A is a graph comparing the fluorescence quenching curves using a 5'-terminal labeled primer (5'-"c"AT-GACGGGTAACGGGGAAT; SEQ ID NO: 24), a universal tagged primer (5'-c"t"ccggcATGACGGGTAACGGG-GAAT; SEQ ID NO: 10); and the increase in fluorescence for a TaqMan® probe (SEQ ID NO: 27).

FIG. 4B is a graph showing the melting curve analysis of a *Cryptosporidium parvum* sequence using a 5'-terminal labeled primer (5'-"c" ATGACGGGTAACGGGGAAT; SEQ ID NO: 24) compared to a universal tagged primer (SEQ ID NO: 10).

FIG. 5 is a graph showing fluorescence quenching curves obtained by real-time quantitative PCR amplification of GE copies of adenovirus 40 using 5'-C"T"CGGCCCGCCGAG-3' (SEQ ID NO: 6) as an exemplary universal tag.

FIG. 7A is a graph showing fluorescence quenching curves obtained by real-time PCR amplification of an adenovirus and a Salmonella sequence using 5'-C"T"CCGGC-3' (SEQ ID NO: 14) as an exemplary universal tag.

FIG. 7B is a graph showing the melting curve analysis using 5'-C"T"CCGGC-3' (SEQ ID NO: 14) as an exemplary universal tag.

FIG. 8A is a graph showing fluorescence quenching curves obtained by real-time RT-PCR amplification of three Hepatitis E Virus genotypes from clinical specimens using 5'-C"T"CCGGC-3' (SEQ ID NO: 14) as an exemplary universal tag.

FIG. 8B is a graph showing the melting curve analysis using 5'-C"T"CCGGC-3' (SEQ ID NO: 14) as an exemplary universal tag.

FIG. 10A shows the use of an exemplary fluorescently labeled UniFluor probe (SEQ ID: 29) having arms (shown in small letters) on either side of the probe region to interact to form a duplex and a single fluorophore (F) attached internally at "t" near the 5' arm. A chemical linker (X) C3 spacer amidite is attached at the end of other side of the arm, which in turn is attached to the forward primer at the 5' end. FIG. 10B shows that when the exemplary fluorescently labeled UniFluor probe (SEQ ID NO: 29) in FIG. 10A is in the absence of the target, the arms interact to form a duplex; the fluorophore in one of the arms (cctc) is quenched by the complimentary arm containing guanosines (ggag) resulting in no fluorescence emission. FIG. 10C shows how the primer part of the UniFluor probe (SEQ ID NO: 29) hybridizes to the target binding region of an exemplary complimentary sequence (SEQ ID NO: 33) during primer extension. FIG. 10D shows how the UniFluor probe (SEQ ID NO: 29) is incorporated into the forward sense strand amplicon and hybridizes with the target binding region of the exemplary complimentary sequence (SEQ ID NO: 34. The reverse primer is shown in SEQ ID NO: 13.

SEQUENCE LISTING

Figure 2A:
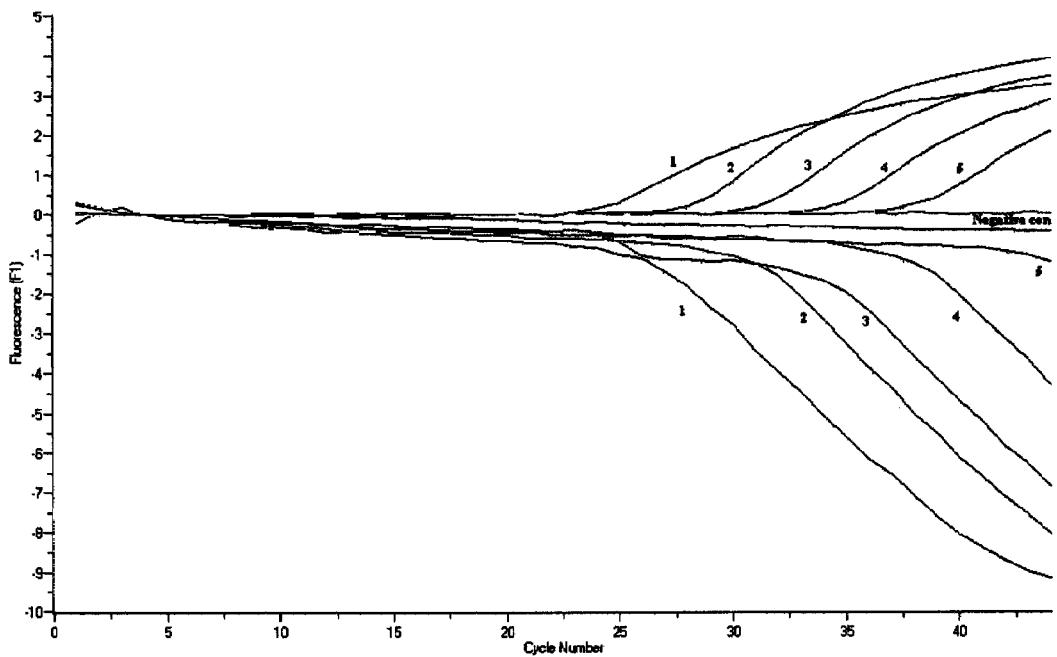
FIG. 2A is a graph showing the concurrent fluorescence visualization of Adenovirus 40 PCR product formation using TaqMan® probe (fluorescence amplification) and the exemplary universal primer of SEQ ID NO: 1 (fluorescence quenching).
Figure 2B:
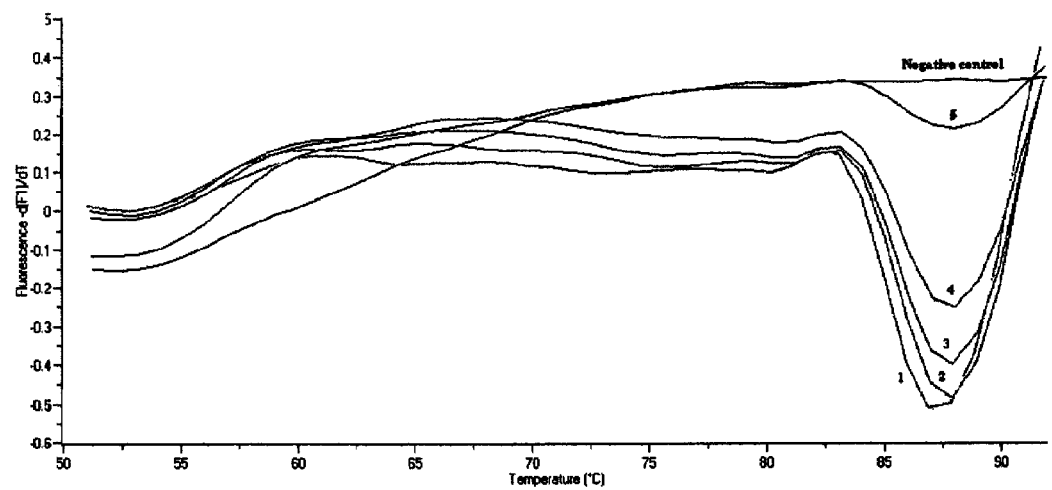
FIG. 2B is a graph showing the melting curve analysis using the exemplary universal primer 5'-C"T"CCGGC (SEQ ID NO: 1).
Figure 2C:
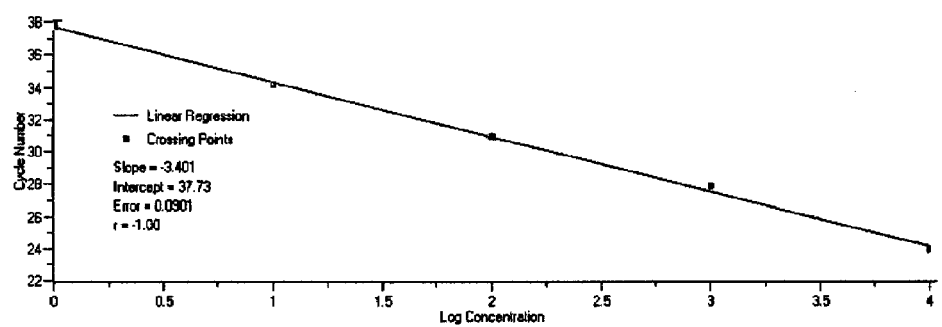
FIG. 2C is a standard curve of hexon based TaqMan® PCR assay of serially diluted adenovirus 40 (FIG. 2A) expressed as cycle number crossing point (CP) versus log concentration of genomic equivalents (GE) per assay ($5 \times 10^4$ to $10^{10}$ GE/assay corresponds to the serial dilution 1 though 5, which are also shown in FIGS. 2A and 2B).

The nucleotide sequences of the nucleic acids described herein are shown using standard letter abbreviations for nucleotide bases. Only one strand of each nucleic acid sequence is shown, but the complementary strand is understood as included by any reference to the displayed strand.

SEQ ID NO: 1 is the nucleic acid sequence of the exemplary universal primer 5'-C"T"CCGGC-3', wherein the "T" is labeled with a detectable label that is altered by hybridization to a complementary sequence.

SEQ ID NOS: 2 and 3 are a forward and a reverse primer for amplification of the hexon protein region of adenovirus, respectively, wherein the forward primer includes the universal primer shown in SEQ ID NO: 1.

SEQ ID NOS: 4 and 5 are a forward and a reverse primer for TaqMan amplification of the hexon protein region of adenovirus, respectively.

SEQ ID NO: 6 is the nucleic acid sequence of the exemplary universal primer 5'-C"T"CGGCCCGCCGAG-3', wherein the "T" is labeled with a detectable label that is altered by hybridization to a complementary sequence.

SEQ ID NO: 7 is the nucleic acid sequence of the exemplary universal primer 5'-C"T"CCX$_{(0-11)}$-3', wherein the "T" is labeled with a detectable label that is altered by hybridization to a complementary sequence.

SEQ ID NOS: 8-12 are forward primers for amplification of a *Cryptosporidium parvum* sequence, wherein the forward primer includes the universal primer shown in SEQ ID NO: 7.

SEQ ID NO: 13 is a reverse primer for amplification of a *C. parvum* sequence.

SEQ ID NO: 14 is the nucleic acid sequence of the exemplary universal primer 5'-C"T"CCGGC-3', wherein the "T" is labeled with a detectable label that is altered by hybridization to a complementary sequence.

SEQ ID NO: 15 is a forward primer for amplification of the hexon protein region of Adenovirus, wherein the forward primer includes the universal primer shown in SEQ ID NO: 14.

SEQ ID NOS: 16 and 17 are a forward and a reverse primer for amplification of a *Salmonella typhimurium* sequence, respectively, wherein the forward primer includes the universal primer shown in SEQ ID NO: 14.

SEQ ID NOS: 18-22 are exemplary universal primers.

SEQ ID NO: 23 is the complementary sequence to the universal primer shown in SEQ ID NO: 1.

SEQ ID NO: 24 is a forward primer labeled at its 5'-terminal nucleotide for amplification of the 18s region of *C. parvum*.

SEQ ID NO: 25 is a TaqMan® probe for amplification of the 18s region of *C. parvum*.

SEQ ID NOS: 26 and 27 are a forward and a reverse primer for amplification of a Hepatitis E Virus sequence, respectively, wherein the forward primer includes the universal primer shown in SEQ ID NO: 14.

SEQ ID NO: 28 is an exemplary universal sequence having less than 50% GC content.

SEQ ID NO: 29 is an exemplary "UniFluor" probe for amplification of the 18s region of *C. parvum*, wherein the probe has a stem and loop structure, a single fluorophore, and a PCR blocker, with the probe being attached to the 5' end of a target-specific primer.

SEQ ID NO: 30 is a sequence complementary to nucleotides 1-8 of SEQ ID NO: 29.

SEQ ID NOS: 31-32 are exemplary universal primers.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

3' end: The end of a nucleic acid molecule that does not have a nucleotide bound to it 3' of the terminal residue.

5' end: The end of a nucleic acid sequence where the 5' position of the terminal residue is not bound by a nucleotide.

Amplifying a nucleic acid molecule. To increase the number of copies of a nucleic acid molecule. The resulting amplification products are called "amplicons."

Array. An arrangement of biological molecules, such as an arrangement of tissues, cells, or nucleic acid molecules, in addressable locations on or in a substrate. The arrangement of molecules within the array can be regular, such as being arranged in uniform rows and columns, or irregular. The number of addressable locations within the array can vary, for example from a few (such as two or three) to more than 50, 100, 200, 500, 1000, 10,000, or more. In certain examples, the array includes one or more molecules or samples occurring on the array a plurality of times (twice or more) to provide an added feature to the array, such as redundant activity or to provide internal controls. A "microarray" is an array that is miniaturized and can in some examples be evaluated or analyzed using microscopy.

Within an array, each arrayed sample or molecule is addressable, such that its location can be reliably and consistently determined within the at least two dimensions of the array. The location or address of each sample or molecule can be assigned when it is applied to the array, and a key or guide can be provided in order to correlate each location with the appropriate target sample or molecule position. Ordered arrays can be arranged in a symmetrical grid pattern or other patterns, for example, in radially distributed lines, spiral lines, or ordered clusters. Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

The sample or molecule addresses on an array can assume many different shapes. For example, substantially square regions can be used as addresses within arrays, but addresses can be differently shaped, for example, substantially rectangular, triangular, oval, irregular, or another shape. The term "spot" refers generally to a localized placement of molecules, tissue or cells, and is not limited to a round or substantially round region or address.

Change: To become different in some way, for example to be altered, such as increased or decreased. A detectable change is one that can be detected, such as a change in the intensity, frequency or presence of an electromagnetic signal, such as fluorescence. In particular examples, the detectable change is a reduction in fluorescence intensity.

Complementary. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In particular examples disclosed herein, the complementary sequence is complementary at a labeled nucleotide, and at each nucleotide immediately flanking the labeled nucleotide.

Fluorophore: A chemical compound, which when excited by exposure to a particular wavelength of light, emits light (fluoresces), for example at a different wavelength of light. Exemplary fluorophores include, but are not limited to: 6-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow, as well as derivatives thereof.

Also encompassed by the term "fluorophore" are luminescent molecules, which are chemical compounds which do not require exposure to a particular wavelength of light to fluoresce; luminescent compounds naturally fluoresce. Therefore, the use of luminescent signals can eliminate the need for an external source of electromagnetic radiation, such as a laser.

A particular type of fluorophore is one whose fluorescence is quenched in the presence of guanine. In one example, fluorescence is quenched by at least 25% in the presence of guanine, such as at least 50%, at least 75%, at least 80%, or at least 90%, as compared to an amount of fluorescence in the absence of guanine (wherein both are in the presence of the appropriate excitation wavelength of light).

Hybridization: Hybridization of a nucleic acid occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acids used. Calculations regarding hybridization conditions required for attaining particular degrees of stringency are discussed in Sambrook et al., *Molecular Cloning: A Laboratory Manual* (Cold Spring Harbor Laboratory Press, Cold Spring Harbor, N.Y., 2001); and Tijssen, *Laboratory Techniques in Biochemistry and Molecular Biology—Hybridization with Nucleic Acid Probes* Part I, Chapter 2 (Elsevier, N.Y., 1993). The $T_m$ is the temperature at which 50% of a given strand of nucleic acid is hybridized to its complementary strand.

For purposes of this disclosure, "stringent conditions" encompass conditions under which hybridization only will occur if there is less than 25% mismatch between the hybridization molecule and the target sequence. "Moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Moderately stringent hybridization conditions are when the hybridization is performed at about 42° C. in a hybridization solution containing 25 mM KPO$_4$ (pH 7.4), 5×SSC, 5×Denhart's solution, 50 µg/mL denatured, sonicated salmon sperm DNA, 50% formamide, 10% Dextran sulfate, and 1-15 ng/1 mL probe (about 5×10$^7$ cpm/µg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM KPO$_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about 5×10$^7$ cpm/µg), while the washes are performed at about 65° C. with a wash solution containing 0.2×SSC and 0.1% sodium dodecyl sulfate.

The complementary nucleic acid sequences disclosed herein can hybridize under stringent, moderately stringent, and highly stringent conditions.

Isolated: An "isolated" biological component (such as a nucleic acid molecule) has been substantially separated, produced apart from, or purified away from other biological components. Nucleic acid molecules which have been "isolated" include nucleic acids molecules purified by standard purification methods, as well as those chemically synthesized. Isolated does not require absolute purity, and can include nucleic acid molecules that are at least 50% isolated, such as at least 75%, 80%, 90%, 95%, 98%, 99% or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part of Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Ligase: An enzyme that can catalyse the joining of two molecules ("ligation") by forming a new chemical bond. An exemplary ligase is DNA ligase, which can link two nucleic acid molecules by forming a phosphodiester bond between the two molecules.

Nucleic acid molecule: A deoxyribonucleotide or ribonucleotide polymer, which can include analogues of natural nucleotides that hybridize to nucleic acid molecules in a manner similar to naturally occurring nucleotides. In a particular example, a nucleic acid molecule is a single stranded (ss) DNA or RNA molecule, such as a primer. In another particular example, a nucleic acid molecule is a double stranded (ds) nucleic acid, such as a target nucleic acid.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

Examples of modified sugar moieties which may be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Ideally, such modifications allow for incorporation of the nucleotide into a growing nucleic acid chain. That is, they do not terminate nucleic acid synthesis.

The choice of nucleotide precursors is dependent on the nucleic acid to be sequenced. If the template is a single-stranded DNA molecule, deoxyribonucleotide precursors (dNTPs) are used in the presence of a DNA-directed DNA polymerase. Alternatively, ribonucleotide precursors (NTPs) are used in the presence of a DNA-directed RNA polymerase. However, if the nucleic acid to be sequenced is RNA, then dNTPs and an RNA-directed DNA polymerase are used.

Primer. A short nucleic acid molecule, such as a DNA oligonucleotide 9 nucleotides or more in length, which in some examples is used to initiate the synthesis of a longer nucleic acid sequence. Longer primers can be about 10, 12, 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example by PCR or other nucleic-acid amplification methods.

The specificity of primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 20, 25, 30, 35, 40, 45, 50 or more consecutive nucleotides.

In one example, a primer includes a label.

Quantitating a nucleic acid molecule: Determining or measuring a quantity (such as a relative quantity) of nucleic acid molecule present, such as the number of amplicons or the number of nucleic acid molecules present in a sample. In particular examples, it is determining the relative amount or actual number of nucleic acid molecules present in a sample.

Quenching of fluorescence: A reduction of fluorescence. For example, quenching of a fluorophore's fluorescence on a universal sequence (or tag or primer) occurs when a quencher molecule (such as guanosine) is present in sufficient proximity to the fluorophore that it reduces the fluorescence signal of the reporter molecule during complimentary strand synthesis.

Real-time quantitative PCR: A method for detecting and measuring products generated during each cycle of a PCR, which are proportionate to the amount of template nucleic acid prior to the start of PCR. The information obtained, such as an amplification curve, can be used to quantitate the initial amounts of template nucleic acid sequence.

Recombinant. A recombinant nucleic acid molecule is one that has a sequence that is not naturally occurring or has a sequence that is made by an artificial combination of two otherwise separated segments of sequence. This artificial combination can be accomplished, for example, by chemical synthesis or by the artificial manipulation of isolated segments of nucleic acid molecules, for example, by genetic engineering techniques.

Sample: Biological samples such as samples containing nucleic acid molecules, such as genomic DNA, cDNA, RNA, mRNA, or combinations thereof. Samples can be obtained from the cells of a subject, such as those present in peripheral blood, urine, saliva, tissue biopsy, surgical specimen, fine needle aspirates, amniocentesis samples and autopsy material.

Sequence specific primer: A nucleic acid sequence that can substantially hybridize with a target nucleic acid molecule, such as under moderately stringent or highly stringent conditions. In particular examples, such primers are at least nine nucleotides long.

Signal: An indicator, such as a detectable physical quantity from which information can be obtained. In one example, a label emits a signal capable of detection, such as a fluorescent signal.

Subject: Living multi-cellular vertebrate organisms, including human and veterinary subjects, such as cows, pigs, horses, dogs, cats, birds, reptiles, and fish.

Synthesis of a nucleic acid molecule: Building up a molecule from its component parts, for example by replicating a nucleic acid molecule. Examples include, but are not limited to, DNA synthesis and RNA-dependent DNA synthesis using reverse transcriptase.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule in a cell (which can include host RNAs (such as mRNA) and DNAs (such as genomic or cDNA), as well as other nucleic acid molecules such as viral, bacterial or fungal nucleic acid molecules), the amplification of which is intended. Purification or isolation of the target nucleic acid molecule, if needed, can be conducted by methods known to those in the art, such as by using a commercially available purification kit or the like.

Universal sequence (or primer or tag): A sequence of nucleotides that do not significantly hybridize to a target nucleic acid molecule and includes a label on the second nucleotide from the 5'-end. In a particular example, a universal tag does not hybridize to a target nucleic acid sequence under moderately or highly stringent conditions. Particular examples of universal tags include, but are not limited to, the sequences shown in SEQ ID NOS: 1, 6, 7, 14, 18-22, and 31-32. In particular examples, universal tags are at least 4 nucleotides in length, such as at least 5, at least 6, at least 7, at least 8, at least 9, at least 10, at least 12, at least 15 or even at least 20 nucleotides. In particular examples, universal tags are 4-100 nucleotides, such as 4-80 nucleotides, 4-60 nucleotides, 5-60 nucleotides, or 5-50 nucleotides.

Nucleic Acid Molecules

Disclosed herein are universal nucleic acid molecules (also referred to herein as universal primers or tags) that can be used in nucleic acid amplification. Although particular universal nucleic acid sequences are provided herein, the disclosure is not limited to these specific examples. The universal tags include a 5'-end, a 3'-end, and a labeled nucleotide. The labeled nucleotide is flanked on both sides by a nucleotide whose complement nucleotides change a detectable signal from the label when the universal tag hybridizes with its complementary nucleic acid molecule. For example, the complementary nucleic acid sequence can contain two or more nucleotides capable of increasing or decreasing a detectable signal from the label in a predictable way. For example, the label on the "T" in the universal sequence 5'-CTCCGGC-3' (SEQ ID NO: 1) is changed when the universal sequence hybridizes to its complementary sequence 3'-GAGGCCG-5' (SEQ ID NO: 23). In particular examples, the universal tag can hybridize to its complementary sequence under high stringency conditions. In other examples the universal sequence is 100% complementary at the labeled nucleotide (such as a "T") and its immediate 3' and 5' nucleotides (such as "C" and "C" or "C" and "G"). In particular disclosed embodiments, the label on the universal sequence is quenched by the complementary sequence, for example particularly effectively quenched by the nucleotides that flank the labeled nucleotide. For example, when the label is a fluorophore (such as 6-FAM) that can be quenched by the G's that hybridize to the C's at the +1 and −1 positions from the labeled nucleotide, the presence of the quenching complements flanking the labeled nucleotide has been found to be particularly effective in quenching the fluorescence signal from the label.

In particular examples, a universal tag includes the sequence 5'-$X_{1(n)}X_2X_3X_4X_{5(n)}$-3', wherein $X_3$ is the labeled nucleotide, wherein $X_2$ and $X_4$ are the nucleotides flanking the labeled nucleotide. $X_{1(n)}$ and $X_{5(n)}$ can be any number of nucleotides, such as zero nucleotides, at least one nucleotide, at least two nucleotides, or 0-15 nucleotides. In particular examples, $X_{1(n)}$ is at least one nucleotide, such as one or more nucleotides, such as 1-20 nucleotides, such as 1-5 nucleotides, and $X_{5(n)}$ is at least two nucleotides, such as at least five nucleotides, at least 10 nucleotides, such as 2-20 nucleotides or 2-15 nucleotides. In other examples, $X_{1(n)}$ is zero nucleotides, and $X_{5(n)}$ is at least four nucleotides, such as at least five nucleotides, at least 10 nucleotides, or 4-25 nucleotides, such as 4-10 nucleotides.

The labeled nucleotide can be at any position in the universal tag, as long as it is flanked on each side by at least one nucleotide whose complement nucleotides change a detectable signal from the label when the universal tag is hybridized with its complementary nucleic acid sequence. In specific examples, the labeled nucleotide in the universal tag is the second nucleotide from the 5'-end. This position can also be referred to as the 0 position. For example, $X_2$ is the nucleotide that is two nucleotides from the 5' end (or the 0 position) in the universal sequence 5'-$X_1X_2X_3X_4X_5$-3'. Similarly, the 0 position of the universal sequences 5'-CTCC$X_{(n)}$ (SEQ ID NO: 18) and 5'-CTCG$X_{(n)}$ (SEQ ID NO: 19) is the "T". Although these examples show the nucleotide containing the label is a thymidine, other nucleotides (for example A, C, G, U, or modified nucleotides such as inosine) can also be labeled using methods known in the art. In particular examples, the labeled nucleotide is a thymidine. In specific examples, the flanking nucleotides are "C", wherein hybridization of the universal tag to the complement nucleotides "G" change the detectable signal.

In a particular example where the labeled nucleotide in the universal tag is the second nucleotide from the 5'-end, the universal tag includes the sequence 5'-$X_2X_3X_4X_{5(n)}$-3', wherein $X_3$ is the labeled nucleotide, wherein $X_2$ and $X_4$ are the two nucleotides flanking the labeled nucleotide, and wherein n is one or more nucleotides, such as at least 2 nucleotides, at least four nucleotides, at least five nucleotides, at least 10 nucleotides, at least 15 nucleotides, such as 1-25 nucleotides, 4-25 nucleotides, 4-15 nucleotides, or 4-12 nucleotides. In particular examples, $X_2$ and $X_4$ are "C". In some examples, $X_3$ is "T". In further examples, $X_3$ is "T" and $X_2$ and $X_4$ are "C".

In one example, a universal nucleic acid sequence includes the sequence 5'-CTCS$X_{(n)}$-3' (SEQ ID NO: 20), wherein $X_{(n)}$ is any number of nucleotides, wherein S is G or C (for example C), and wherein T is labeled. In particular examples, $X_{(n)}$ is 3-50 nucleotides, such as 3-20 nucleotides, or 3-11 nucleotides. In more particular examples $X_{(n)}$ is at least 3 nucleotides, such as 3 nucleotides, such as no more than 50 nucleotides. In another example, a universal nucleic acid sequence includes the sequence 5'-CTCSXXX-3' (SEQ ID NO: 21), wherein X is any nucleotide, wherein S is G or C, and wherein T is labeled. For example, the universal nucleic acid sequence can include the sequence 5'-CTCCGGC-3' (SEQ ID NO: 14), as well as the sequences shown in SEQ ID NO: 1, 6, 7, 18, 19, or 22. wherein T is the labeled nucleotide. Another exemplary universal tag includes the sequence 5'-CTCSXXX$_{(n)}$-3' (SEQ ID NO: 22), wherein a fluorophore is attached to "T" and n is 0-11 nucleotides, such as 1-11 nucleotides, such as at least one nucleotide.

The change in the detectable signal from the label upon hybridization of the universal tag with its complementary sequence can be an increase or a decrease in the detectable signal, such as an increase or decrease of at least 10%, such as at least 20%, at least 50%, at least 75%, or at least 90%, as compared to a control, such as an amount of signal when the universal tag is not hybridized to its complementary sequence (for example when it is unbound in solution). In examples in which the label is a fluorescent label, the intensity of the fluorescence emitted by the label changes in a predictable way (for example by decreasing or dissipating when the universal sequence hybridizes to its complementary sequence). In particular examples, the change in signal is a decrease in fluorescence, such as a quenching of fluorescence. For example, the fluorescence can decrease by at least 10%, such as at least 20%, at least 50%, at least 75%, or at least 90%, when the universal tag is hybridized to its complementary sequence, as compared to a control, such as an amount of fluorescence when the universal tag is not hybridized to its complementary sequence.

In particular examples, when the universal tag hybridizes to its complementary sequence, a guanosine (G) on the complementary strand decreases the signal from the fluorophore, such as decrease fluorescence of at least 10%, such as at least 50% or at least 90%. Guanosine serves as an electron donor and therefore can be used to quench a fluorophore.

In particular examples, the label is a fluorophore, such as a fluorophore whose signal is increased or decreased in the presence of a particular nucleotide or combination of nucleotides. In a specific example, the fluorophore signal is decreased or quenched in the presence of a nucleotide, such as a nucleotide with fluorescent quenching abilities (such as G or isoG). In one example, the fluorophore is one that is decreased in the presence of G or isoG. The signal can be decreased by any detectable amount, such as at least 10%, at least 30%, at least 50%, at least 90%, and so on. Particular examples of fluorophores that can be used to label a nucleotide in the universal tags of the present application, include, but are not limited to, 6-FAM; 5-FAM; BODIPY; TAMRA; acridine; stilbene; HEX; TET; ROX; Texas Red; JOE; Cy3; Cy5; VIC; LC Red 640; LC Red 705; Yakima yellow; as well as derivatives thereof.

The disclosed universal tags can be any length that permits detection of a change in signal from the label on the tag, when the universal tag hybridizes with its complementary sequence. In particular examples, the universal nucleic acid sequence is at least 4 nucleotides, at least 5 nucleotides, at least 7 nucleotides, at least 10 nucleotides, at least 11 nucleotides, at least 12 nucleotides, at least 15 nucleotides, such as 4-25 nucleotides, 5-25 nucleotides, 7-25 nucleotides, 11-25 nucleotides, 15-25 nucleotides, 4-15 nucleotides, 5-15 nucleotides, or 7-15 nucleotides.

In particular examples the disclosed universal tags include primarily "C" and "G" nucleotides. In some examples, at least 50% of the nucleotides present in a universal tag can be "C" or "G" nucleotides (that is, they have at least a 50% GC content), such as at least 60%, at least 75%, at least 80%, at least 85%, at least 90%, at least 95%, at least 98% or even at least 99% GC content. For example, the universal sequence 5'-CTCCGGC-3' (SEQ ID NO: 14) has about an 86% GC content (6 of 7 nucleotides) and the universal sequence 5'-C"T"CGGCCCGCCGAG-3' (SEQ ID NO: 6) has about an 87% GC content (13 of 15 nucleotides). In addition, universal tags with GC content of less than 50% can also be used (such as the universal sequence 5'-C"T"CCATA; SEQ ID NO: 28).

The disclosed universal tags can be linked to a sequence-specific primer sequence, thereby labeling the sequence-specific primer sequence. For example, the 3'-end of the universal tag can be ligated to the 5'-end of a forward or a reverse sequence-specific primer. The labeled sequence-specific primer can then be used in an amplification reaction, such as an RT-PCR reaction. The sequence-specific primer can recognize a target nucleic acid of interest, such as a pathogen nucleic acid sequence, for example a viral, fungal, bacterial, or parasitic DNA or RNA sequence. In another example, a target nucleic acid sequence, such as a DNA or RNA sequence, is a nucleic acid sequence whose expression is altered in response to a disease, such as cancer. The sequence-specific primer can be any length that permits amplification of the desired nucleic acid molecule. In particular examples, a sequence-specific primer is at least six nucleotides, such as at least 9, at least 10, at least 12, at least 15, at least 20, at least 25, at least 30, at least 35, at least 40 or even at least 50 nucleotides.

Methods of Nucleic Acid Amplification

The disclosed universal tags can be used in any nucleic acid amplification reaction to determine whether a particular target nucleic acid sequence is present, such as a DNA or RNA molecule. For example, methods are disclosed for detecting a target nucleic acid molecule. In particular examples, the method includes incubating a sample containing nucleic acids with a universal tag linked to a forward or a reverse target sequence specific primer, and with a corresponding forward or reverse target sequence specific primer not containing the universal tag. In other examples, both the forward and the reverse target sequence contain a universal tag. As described above, the 3'-end of the universal primer can be ligated to the 5'-end of the sequence specific primer.

The sample and labeled forward and a reverse primer not containing the universal tag, or a forward primer not containing the universal tag and a labeled reverse primer, are incubated under conditions sufficient to permit amplification of the target nucleic acid. For example, the reaction can include dNTPs, a polymerase, and $MgCl_2$.

Any primer extension amplification method can be used. Particular examples include, but are not limited to: real-time PCR (for example see Mackay, *Clin. Microbiol. Infect.* 10(3): 190-212, 2004), Strand Displacement Amplification (SDA) (for example see Jolley and Nasir, *Comb. Chem. High Throughput Screen.* 6(3):235-44, 2003), self-sustained sequence replication reaction (3SR) (for example see Mueller et al., *Histochem. Cell. Biol.* 108(4-5):431-7, 1997), ligase chain reaction (LCR) (for example see Laffler et al., *Ann. Biol. Clin.* (Paris).51(9):821-6, 1993), transcription mediated amplification (TMA) (for example see Prince et al., *J Viral Hepat.* 11(3):236-42, 2004), or nucleic acid sequence based amplification (NASBA) (for example see Romano et al., *Clin. Lab. Med.* 16(1):89-103, 1996). For example, NASBA can be performed using the universal tags disclosed herein by substituting one NASBA primer with a universal tag while the other primer contains the RNA polymerase promoter. The promoter sequence, located on the 5' tail of the second primer, generates RNA copies complementary to the universal tag. This sequence will hybridize to the universal tag and RNA transcriptase will extend the universal tag extension product. This universal tag RNA is degraded by RNase H, releasing the fluorescence (similar to hydrolysis of TaqMan probes). As the production of more RNA proceeds, this process will increase of the fluorescence signal due to the activity of RNase H.

A change in detectable signal from the label on the universal tag is monitored, wherein a change in signal indicates the presence of the target nucleic acid sequence, and wherein no significant change in signal indicates that the target nucleic acid molecule is not present in the sample. The change in signal can be compared to a signal present earlier, such as prior to nucleic acid amplification. The detectable signal changes in a predictable manner that permits determination of whether or not a target nucleic acid sequence is present in a sample, and in some examples, quantitation of an amount of target nucleic acid sequence is present in a sample. For example, when the label is a fluorophore that can be quenched by guanosine, and the two flanking nucleotides are "C", the "Gs" present on the complementary strand will quench the fluorophore in a predictable manner, wherein a reduction in fluorescent signal during nucleic acid amplification indicates that the target nucleic acid sequence is present in a sample, while no substantial reduction in fluorescent signal during nucleic acid amplification indicates that the target nucleic acid sequence is not present in a sample.

In some examples, the change in signal is monitored during the amplification reaction, for example in real time as the amplicons are formed. For example, the label present on the universal tag will generate a significant signal or not, when the primers are freely floating in the nucleic acid amplification reaction mixture. During nucleic acid amplification, when polymerase creates nucleic acid amplicons, the primer, including the labeled universal tag, is incorporated into the amplicon. The signal from the label will increase or decrease due to its incorporation into the double-stranded amplicon molecule. As more amplicons are produced during nucleic acid amplification, the overall signal of the reaction mixture will increase or decrease. The change in signal can be monitored using any commercially available system. This change in signal permits detection of a target nucleic acid sequence in the reaction.

In one example where the label is a fluorophore, the change in signal monitored during the amplification reaction is a decrease in fluorescence. The fluorescence of the dye is only slightly quenched (or not quenched at all) when the primers are freely floating in the nucleic acid amplification reaction mixture. During nucleic acid amplification, when polymerase creates nucleic acid amplicons, the primer, including the fluorescently labeled universal tag, is incorporated into the amplicon. The fluorescence of the incorporated primer decreases several fold due to quenching of the dye signal by its incorporation into the double-stranded amplicon molecule and proximity to guanosine (or other quenching molecule, such as isoG) on the complementary strand. As more amplicons are produced during nucleic acid amplification, the overall fluorescence of the reaction mixture decreases. The decrease in fluorescence can be measured and observed, for example by using a commercially available nucleic acid amplification system capable of measuring fluorescence (such as real-time PCR thermocyclers). A decrease in fluorescent signal indicates the presence of a target nucleic acid sequence in the reaction.

In other or additional examples, the change in signal is monitored after the amplification, for example by exposing the resulting amplicons to a melting procedure to denature the double-stranded amplicons. During the denaturation, a change in signal is detected. The resulting signal peaks, such as fluorescence peaks, can differentiate polymorphisms in the nucleic acid amplicons. Therefore, melting curve analysis can be used to confirm the presence of a target nucleic acid sequence, and can also be used to distinguish polymorphisms in amplicons.

In other examples, the change in signal that is monitored during the amplification reaction is an increase in fluorescence. In this example, the probe includes a stem and loop structure, wherein the stem represents the non-target nucleic acid sequence (which contains a single internal fluorescent label that remains quenched with its complimentary stem part). However, during target-dependent synthesis, a complimentary strand is synthesized and the probe hybridizes to the amplicon.

In other examples, the probe oligonucleotides are structured such that the fluorophore is quenched by another quenching fluorophore and emits fluorescence upon oligonucleotide probe hybridization to a target nucleic acid. Examples of these types of probe structures include: Scorpion probes (for example see Whitcombe et al., *Nature Biotech.* 17:804-7, 1999; U.S. Pat. No. 6,326,145, the disclosure of which is herein incorporated by reference), Sunrise probes (for example see Nazarenko et al., *Nuc. Acids Res.* 25:2516-21, 1997; U.S. Pat. No. 6,117,635, the disclosure of which is herein incorporated by reference), and Molecular Beacons (Tyagi et al., *Nature Biotech.* 14:303-8, 1996; U.S. Pat. No. 5,989,823, the disclosure of which is incorporated herein by reference). In many of these probe structures, the stem part is not internally labeled with 6-carboxyfluorescein and uses an additional quenching fluorophore in the complimentary stem portion.

In other or additional examples, the change in signal monitored during the amplification reaction is an increase in fluorescence. In this example, the universal primer remains single-stranded in the absence of the target nucleic acid molecule, and is not acted upon by a restriction endonuclease, such as BstI. However, during target-dependent synthesis, a complementary strand is synthesized and becomes nickable by the restriction endonuclease. The cleavage cuts the fluorescent-labeled primer, thereby separating it from the complimentary quencher, such as guanosine. This results in an increase in fluorescence signal.

Methods of detecting a target nucleic acid molecule following nucleic acid amplification are provided. The methods include incubating a sample containing or thought to contain the target nucleic acid molecule with a forward primer and a reverse primer that are specific for the target nucleic acid molecule. Either the forward primer or the reverse primer is linked at its 5' end to the 3' end of a universal tag, under conditions sufficient to allow amplification of the target nucleic acid molecule (such as real-time PCR conditions). However, in some examples, both the forward and the reverse primer are linked at their 5' ends to the 3' end of a universal tag. The amplification results in the generation of a labeled amplicon. The amplicon is exposed to conditions that permit denaturation of the amplicon into single strand nucleic acid molecules, and then exposed to conditions that permit rehybridization of the strands. During the annealing step, the universal primer is incorporated into a double stranded nucleic acid molecule, incorporating quencher nucleotides (such as Gs) in a region complimentary to the label on the universal tag sequence. This results in a change in detectable signal, for example relative to the detectable signal from the label before the formation of double stranded DNA. A change in signal indicates that the target nucleic acid molecule is present in the sample, and no significant change in signal indicates that the target nucleic acid molecule is not present in the sample.

In addition to determining whether a particular target nucleic acid molecule is present, the method can further include quantifying the target nucleic acid molecule. In one example quantitation includes comparing a signal to an amount of signal from a known amount of nucleic acid.

Samples containing nucleic acid molecules can be obtained from any appropriate specimen, for instance blood or blood-fractions (such as serum). Techniques for acquisition of such samples are well known in the art (for example see Schluger et al. *J. Exp. Med.* 176:1327-33, 1992, for the collection of serum samples). Serum or other blood fractions can be prepared in the conventional manner. For example, about 200 µL of serum can be used for the extraction of DNA for use in amplification reactions.

Once a sample has been obtained, the sample can be used directly, concentrated (for example by centrifugation or filtration), purified, or combinations thereof. In one example, DNA is prepared from the sample, yielding a nucleotide preparation that is accessible to, and amenable to, nucleic acid amplification. Similarly, RNA can be prepared using a commercially available kit (such as the RNeasy Mini Kit, Qiagen, Valencia, Calif.).

Kits

The present disclosure provides kits that include one or more disclosed universal tags. The kits can further include ligase, to permit ligation of the universal tag to the 5'-end of a forward or a reverse target sequence-specific primer.

In some examples, the kit also includes one or more forward or reverse target sequence-specific primers, such as forward and reverse primers that recognize a specific pathogen or a specific nucleic acid sequence whose expression is changed in response to a disorder. For example, the kit can include forward and reverse primers that can be used to amplify the nucleic acid sequence of a particular pathogen, such as a viral, bacterial, parasitic, or fungal target nucleic acid sequence. In one example, the forward and reverse primers can be used to amplify a particular human nucleic acid sequence, such target nucleic acid sequence associated with a disease, such as cancer. In particular examples, forward and reverse primers hybridize to a target sequence under highly stringent hybridization conditions. In some examples, the universal tag in the kit is already attached to the 5'-end of the forward or reverse primer. In other examples, the universal tag in the kit is separate from the forward or reverse primer, and can be ligated to the forward or reverse primer by a user.

Arrays

The present disclosure provides arrays that include one or more of the disclosed universal tags. Such arrays can be used to detect the presence or absence of one or more target nucleic acid sequences, or to detect a change in expression of one or more target nucleic acid sequences.

Such arrays can include nucleic acid molecules, such as DNA or RNA molecules. The nucleic acid sequences attached to the array can be directly linked to the support. Alternatively, the nucleic acid sequences can be attached to the support by other nucleotide sequences, such as sequences or other molecules that serve as spacers or linkers to the solid support. The length of each nucleic acid molecule attached to an array can be selected to optimize binding of target nucleic acid sequences. An optimum length for use with a particular nucleic acid sequence can be determined empirically. In one example, nucleic acid molecules attached to an array are at least 15 nucleotides, such as at least 20 nucleotides, such as from about 20 to about 35 nucleotides in length or about 25 to about 40 nucleotides in length. The nucleic acid molecules can be bound to a support by either the 3' end of the nucleic acid molecule or by the 5' end of the nucleic acid molecules. In general, the internal complementarity of an oligonucleotide probe in the region of the 3' end and the 5' end determines binding to the support.

In one example, the amino group of one or more target nucleic acid sequences, such as a nucleic acid sequence found in a pathogen or associated with a particular disease, is attached via its 5' end to the surface of a solid support. Ideally, such target nucleic acid sequences can hybridize to an amplicon containing a universal tag. The array can also include one or more control nucleic acid sequences (such as a housekeeping gene) attached to the surface of a solid support.

The methods and apparatus in accordance with the present disclosure takes advantage of the fact that under appropriate conditions nucleic acid molecules attached to an array can form base-paired duplexes with nucleic acid molecules exposed to the array that have a complementary base sequence. The stability of the duplex is dependent on a number of factors, including the length of the nucleic acid molecules attached to an array, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences attached to the array and the sequences incubated with the array. By carrying out the hybridization at temperatures close to the expected $T_m$'s of the type of duplexes expected to be formed between the target sequences and the oligonucleotides bound to the array, the rate of formation of mismatched duplexes can be reduced.

The solid support can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567, herein incorporated by reference).

In general, suitable characteristics of the material that can be used to form the solid support surface include: being amenable to surface activation such that upon activation, the surface of the support is capable of covalently attaching a biomolecule such as a nucleic acid sequence thereto; amenability to "in situ" synthesis of biomolecules; being chemically inert such that at the areas on the support not occupied by nucleic acid sequences are not amenable to non-specific binding, or when non-specific binding occurs, such materials can be readily removed from the surface without removing the nucleic acid sequences.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

A wide variety of array formats can be employed in accordance with the present disclosure. One example includes a linear array of nucleic acid sequence bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185, herein incorporated by reference). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Biaxially oriented polypropylene (BOPP) films can also be used, for example to reduce background fluorescence.

The array formats of the present disclosure can be included in a variety of different types of formats. A "format" includes any format to which the solid support can be affixed, such as microtiter plates, test tubes, inorganic sheets, dipsticks, and so forth. For example, when the solid support is a polypropylene thread, one or more polypropylene threads can be affixed to a plastic dipstick-type device; polypropylene membranes can be affixed to glass slides. The particular format is, in and of itself, unimportant. All that is needed is a solid support to which nucleic acid molecules can be affixed thereto without affecting the functional behavior of the solid support or any nucleic acid molecule absorbed thereon, and that the format (such as the dipstick or slide) is stable to any materials into which the device is introduced (such as clinical samples and hybridization solutions).

Arrays can be prepared by a variety of approaches. In one example, nucleic acid sequences are synthesized separately and then attached to a solid support (see U.S. Pat. No. 6,013, 789, herein incorporated by reference). In another example, nucleic acid sequences are synthesized directly onto the support to provide the desired array (see U.S. Pat. No. 5,554,501, herein incorporated by reference). Suitable methods for covalently coupling nucleic acid sequences (such as oligonucleotides) to a solid support and for directly synthesizing nucleic acid sequences onto the support are known to those in the art (for example see Matson et al., *Anal. Biochem.* 217: 306-10, 1994). In one example, nucleic acid sequences are synthesized onto the support using conventional chemical techniques for preparing nucleic acid sequences on solid supports (such as see PCT applications WO 85/01051 and WO 89/10977, or U.S. Pat. No. 5,554,501, herein incorporated by reference).

Detection of Nucleic Acid Molecules

The presence of a target nucleic acid in a sample can be determined. In addition, changes in expression of one or more target nucleic acids can also be determined. The present disclosure is not limited to particular methods of detection. Any method of detecting a nucleic acid molecule can be used, such as physical or functional assays.

In one example, the disclosed method includes amplifying a target nucleic acid molecule using the universal tags disclosed. For example, a target nucleic acid molecule can be amplified using a forward primer containing a universal tag, and a reverse primer containing a label, such as a fluorophore, such as Cy5 or Cy3, for example using the methods described above. Methods for labeling nucleic acid molecules such as primers are well known. If the target nucleic acid molecule is present, a labeled amplicon containing the label from the forward and reverse primers will be generated. In a particular example, labeled forward and labeled reverse primers are used to amplify a target nucleic acid sequence obtained from a subject, such as a subject having or suspected of having an infection or a disease. Those skilled in the art will appreciate that amplification can directly be performed on an array, for example by using a universal primer attached to the array. The anchored universal primer permits simultaneous capture, amplification and detection when the microarray is incubated with sample nucleic acid molecules (such as DNA or RNA) and the appropriate primer (for example see U.S. Pat. No. 6,531,302, herein incorporated by reference).

The resulting labeled amplicon can be incubated with an array containing target nucleic acid molecules attached thereto under conditions that permit hybridization of the amplicon with the target nucleic acid molecules on the array. In one example, a pre-treatment solution of organic compounds, solutions that include organic compounds, or hot water, can be applied before hybridization (see U.S. Pat. No. 5,985,567, herein incorporated by reference). Hybridization conditions for a given combination of nucleic acid molecules can be optimized routinely in an empirical manner close to the $T_m$ of the expected duplexes, thereby increasing sensitivity of the method. Identification of the location in the array, such as a cell, in which binding occurs, permits a rapid and accurate identification of target nucleic acid sequences present in the amplified material. Detection of the signal from the amplicon on the array indicates that the target nucleic acid sequence is present in the sample, and can be used to confirm results obtained during the amplification reaction. In contrast, when no significant increase is detected, this indicates that the target nucleic acid molecule is not present in the sample.

Detecting a hybridized complex on an array has been previously described (see U.S. Pat. No. 5,985,567, herein incorporated by reference). In one example, detection includes detecting one or more labels present on the amplicon hybridized to the target nucleic acid molecule. In particular examples, the method further includes quantification, for instance by determining the amount of hybridization, for example relative to a control (such as a known amount of nucleic acid molecule).

Example 1

Comparison to TaqMan® Assay

This example describes methods used to compare the TaqMan® assay to the method of the present disclosure which uses the disclosed universal primers. Adenovirus 40 was used as a model system; however one skilled in the art will appreciate that similar methods can be used to amplify any target nucleic acid molecule of interest using the disclosed universal nucleic acid molecules.

The primers were prepared as follows. The universal sequence 5'-C"T"CCGGC-3' (SEQ ID NO: 1) (a universal primer that does not specifically bind to a target sequence, such as adenovirus sequences.) was synthesized and attached to the 5'-end of an adenovirus-specific primer as follows. "T" refers to the position where 6-carboxyfluorescein was incorporated. Fluorescent oligodeoxyribonucleotides were synthesized on a Biosystems DNA synthesizer through the direct incorporation of the C5-fluorescein-dT phosphoramidite to the "T". The modified forward primer 5'-C"T"C CGG C GGA CGC CTC GGA GTA CCT GAG (AdJVF; SEQ ID NO: 2) which includes the labeled hairpin oligonucleotide (SEQ ID NO: 1), and reverse primer 5'-AC IGT GGG GTT TCT GAA CTT GTT (AdJVR; SEQ ID NO: 3) were designed to amplify the hexon protein region to a 96-bp fragment to specifically detect adenovirus species. The oligonucleotides were synthesized and used without further purification.

Figure 9A:
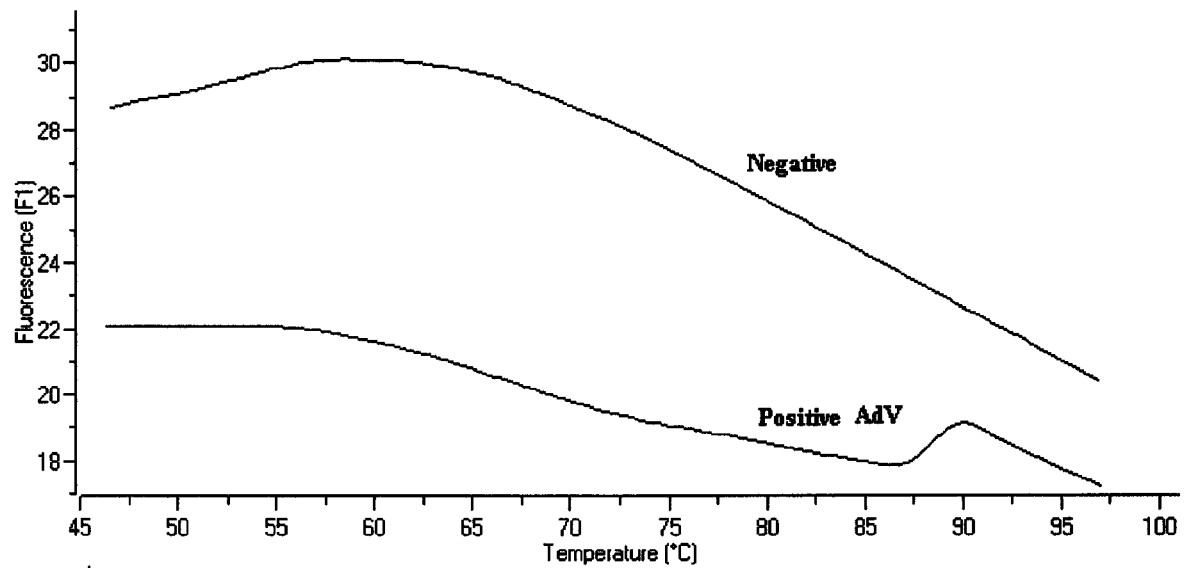
FIG. 9A is a graph showing the increase in fluorescence during melting curve analysis of an adenovirus 40 PCR product produced using 5'-C"T"CCGGC-3' (SEQ ID NO: 14) as an exemplary universal tag.
Figure 9B:
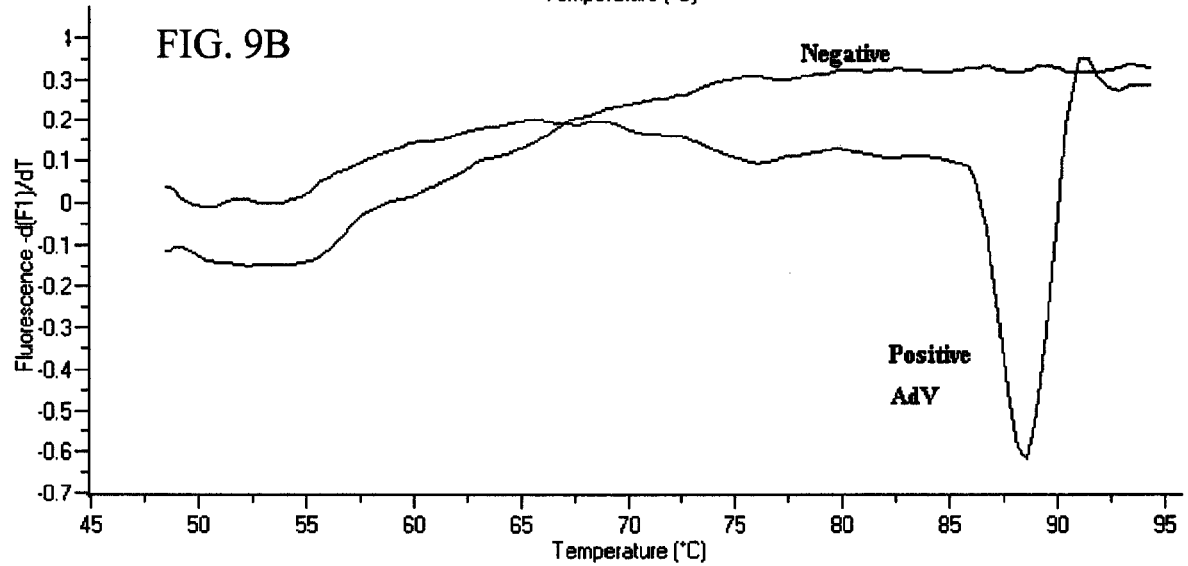
FIG. 9B is a graph showing the melting curve analysis of an adenovirus 40 sequence using 5'-C"T"CCGGC-3' (SEQ ID NO: 14) as an exemplary universal tag. Plotting melting peaks were derived based on the R.A.P.I.D. System software (Idaho Technology, Inc.; Salt Lake City, Utah) by plotting the negative derivative of fluorescence over change in temperature versus temperature (−dF/dT vs. T).

The real-time PCR assay was performed using the QuantiTect™ Probe PCR kit (Qiagen, USA) and a R.A.P.I.D. System real-time PCR thermal cycler (Idaho Technology, Salt Lake City, Utah). Amplification reactions contained 2 µL template DNA, 0.25 mM primers (SEQ ID NOS: 2 and 3), in a final reaction volume of 20 µL. The protocol took approximately 90 minutes to complete with the following PCR conditions: hot-start denaturation step at 95° C. for 15 minutes, followed by 45 cycles with a 95° C. denaturation for 10 seconds, 55° C. annealing for 45 seconds and 72° C. elongation for 15 seconds. Following the amplification, a melting curve was acquired by heating the product at 20° C./second to 95° C., cooling it at 20° C./second to 45° C., keeping it at 45° C. for 20 seconds, and then slowly heating it at 0.1° C./second to 95° C. Fluorescence signal (F) was measured through the slow heating phase (T). During melting curve analysis, the fluorescence increases upon separation of the PCR product strands, with a maximum peak at the characteristic $T_m$ of the product (FIG. 9A). As the software for all commercially-available real-time PCR systems visualizes melting curve data using the negative derivative of fluorescence over change in temperature versus temperature (−dF/dT vs. T), the melting curve data generated when using the exemplary universal primer is shown as a "dip" at the characteristic $T_m$ of the product (FIG. 9B). All amplifications reactions were carried out in duplicate. Amplicons were visualized by agarose gel electrophoresis and ethidium bromide staining to confirm the specificity of PCR products.

As shown in FIGS. 1A and 1B, use of these primers to amplify an Adenovirus sequence results in the addition of a 3'-GAGGCCG-5' (SEQ ID NO: 23) sequence to the amplified sequence. This sequence is the reverse complement of the universal primer sequence, and will reduce the fluorescence of the fluorophore on the "T" of the universal primer when the two strands hybridize. This reduction of fluorescence can be monitored, wherein the presence of reduced fluorescence indicates that the target sequence of interest (here the gene for adenovirus hexon protein) is present.

The sensitivity of the TaqMan® assay for adenovirus 40 (AdV40) was determined using genomic equivalent (GE) copies. Specified regions of the genome were amplified and cloned, and the plasmids used as GE copies. Amplification of the hexon region of AdV40 was carried out with the forward primer 5'-TGGCCACCCCCTCGATGA-3' (position # 2-19; SEQ ID NO: 4) and reverse primer 5'-TTTGGGGGCCAGG-GAGTTGTA-3' (position # 381-361; SEQ ID NO: 5) of GenBank Accession No. X51782. The PCR products were cloned into a pDrive cloning vector using a Qiagen PCR Cloning$^{plus}$ Kit (Qiagen, Valencia, Calif.). DNA sequences of the cloned products were determined with the BigDye terminator cycle sequence kit and ABI 377A sequencer (Applied Biosystems). Plasmids were purified using the Nucleobond 100 kit (Promega).

As shown in FIG. 2A, a comparison of using the TaqMan® assay to amplification using the disclosed universal primers demonstrates that both assays produce similar crossing thresholds over 5 $\log_{10}$ dilutions (50 000, 5000, 500, 50 and 5 GE copies per reaction). In addition, comparison of the TaqMan® assay with the universal primer shows that quantitation can be performed because the quenching rate corresponds to the initial starting copy numbers of the template DNA. As shown in FIG. 2B, the universal primer permits detection at as low as 5 copies of a nucleic acid molecule per reaction.

The quantitative TaqMan® assay, currently the "gold standard" for real-time PCR, was used to determine the sensitivity of detection for AdV40. The quantitative assay presented in FIG. 2C shows the detection limit of AdV40 to five GE copies. This same level of sensitivity was achieved using the disclosed universal primers. Therefore, the disclosed methods and universal primers provide the same detection sensitivity of the TaqMan® assay.

The unknown concentration of a nucleic acid molecule can be quantified through a quantitative analysis of the method using a 10-fold serial dilution of a known amount of initial DNA template sample (FIG. 3A) and corresponding the quenching rate at each cycle can be calculated. No fluorescence decline in the negative samples were observed even after 45 cycles (FIG. 3A) and negative samples showed no peak in melting curve analysis (FIG. 3B).

Those skilled in the art will understand that the amount of target nucleic acid present can be quantitated, for example using software that calculates crossing points similar to the fluorescence increase. It is also possible to quantitate an amount of target nucleic acid present, for example by calculating the crossing points and fluorescence followed by regression analysis to determine the quantity.

Example 2

Comparison of Universal Tags to Primers Labeled at the Terminal 5'-End

This example describes methods used to compare the effects of using a primer labeled at its very 5'-end, to the disclosed universal primers. The protozoan parasite, *Cryptosporidium parvum*, was used as a model system; however one skilled in the art will appreciate that similar methods can be used to amplify any target nucleic acid molecule of interest using the disclosed universal nucleic acid molecules.

The primers were prepared as follows. The universal sequence 5'-C"T"CCGGC-3' (SEQ ID NO: 1) (a universal primer that does not specifically bind to a target sequence, such as *Cryptosporidium* sequences) was synthesized and attached to the 5'-end of a *Cryptosporidium*-specific primer as described in Example 1. The modified forward primer which includes SEQ ID NO: 1 (5'-C"T"CCGGCATGACGGG-TAACGGGGAAT, SEQ ID NO: 10) and the reverse primer (5'-CCAATTACAAAACCAAAAAGTCC-3'; SEQ ID NO: 13) were designed to amplify the conserved partial sequence of the 18S ribosomal RNA to a 159-bp fragment to specifically detect *Cryptosporidium* species. The oligonucleotides were synthesized and used without further purification.

The real-time PCR assay was performed using SEQ ID NOS: 10 and 13 using the methods described in Example 1. Following the amplification, a melting curve was acquired using the methods described in Example 1.

Use of SEQ ID NO: 10 to amplify *Cryptosporidium* sequence results in the addition of a 3'-GAGGCCG-5' (SEQ ID NO: 23) sequence to the amplified sequence. This sequence is the reverse complement of the universal primer sequence, and will reduce the fluorescence of the fluorophore on the "T" of the universal primer when the two strands hybridize. This reduction of fluorescence can be monitored, wherein the presence of reduced fluorescence indicates that the target sequence of interest (here the *Cryptosporidium* 18S sequence) is present.

The results obtained using the disclosed universal primer were compared to use of a sequence-specific forward primer directly labeled on its 5' nucleotide using the same amount of DNA. Amplification of the 18S region of *Cryptosporidium* was performed with the forward primer 5'-"C"ATGACGGG-TAACGGGGAAT-3' (SEQ ID NO: 24) wherein the "C" included a fluorophore, and reverse primer (SEQ ID NO: 10) was performed as described in Example 1.

As shown in FIG. 4A, a comparison of using the 5'-end fluorescent labeling primer to amplification using the disclosed universal primers demonstrates that the universal primer results in quenching that corresponds to the same crossing point as observed for the TaqMan® assay. However, the fluorescent primer labeled at the very terminal 5'-end (SEQ ID NO: 24) produced no detectable signal during amplification (FIG. 4A) or during melting curve analysis (FIG. 4B) that indicated the presence of the target sequence.

Example 3

Amplification of Pathogen Sequences Using $CTCGX_{(10)}$

This example describes methods using the disclosed universal primers to amplify and detect pathogens. Although this example describes amplification of adenovirus sequences using another exemplary universal tag with the sequence 5'-C"T"CGGCCCGCCGAG-3' (SEQ ID NO: 6), the disclosed methods and universal primers can be used to amplify any nucleic acid molecule of interest.

The primers shown in Table 1 were generated as described in Example 1. The "T" two nucleotides from the 5'-end of the primer (shown in quotation marks in Table 1) was labeled with 6-carboxy fluorescein as described in Example 1.

TABLE 1

Forward primers including a universal primer CTCGX(0).

| Microbe | Forward primer (SEQ ID NO:)* | Reverse primer (SEQ ID NO:) |
|---|---|---|
| Adenovirus | c"t"cggcccgccgagGACGCCTCGGA GTACCTGAG (5) | 5'-ACIGTGGGGTTTCTGAACTTGTT (3) |
| Norovirus | c"t"cggcccgccgagTCAGCACTTCT ACCAAGAAGCAGC (7) | GCCTCAAACAGAACGCTACCTGT (8) |

*Universal primer sequence shown in lowercase; sequence-specific primer shown in uppercase.
"T" includes 6-carboxy fluorescein.

The adenovirus hexon protein region sequence was amplified using PCR with SEQ ID NOS: 5 and 3 as follows. The real-time PCR assay and melting curve analysis was performed as described in Example 1.

As shown in FIG. 5, as the concentration of the plasmid copies increase, the quenching of the fluorescence signal occurs at progressively earlier PCR cycles, and is directly proportional to the copy numbers. The detection limit shown (8 copies of adenovirus DNA) demonstrates the sensitivity of the assay using the disclosed universal primers.

Therefore, the rate of fluorescence quenching can be controlled by varying the length of the universal tag. The melting curve analysis of the product produced in these reactions is shown in FIG. 6B.

Example 4

Amplification of Pathogenic Sequences Using CTCCX$_{(0-11)}$

This example describes methods used to amplify a *C. parvum* 18S rRNA gene sequence using exemplary universal tags with the sequence 5'-C"T"CCX$_{(0-11)}$ (SEQ ID NO: 7) attached to the 5'-end of an appropriate target sequence-specific primer.

The primers shown in Table 2 were generated as described in Example 1. The "T" two nucleotides from the 5'-end of the primer (shown in quotation marks in Table 2) was labeled with 6-carboxy fluorescein as described in Example 1.

Example 5

Amplification of Pathogen Sequences Using CTCCGGC

This example describes methods used to amplify AdV40, *Salmonella choleraesuis* serovar *Typhimurium* (*S. typhimurium*), *C. parvum*, and Hepatitis E Virus sequences using an exemplary 7-mer universal tag with the sequence 5'-C"T"C-CGGC-3' (SEQ ID NO: 14), attached to the 5'-end of an appropriate sequence-specific primer.

The primers shown in Table 3 were generated as described in Example 1. The "T" two nucleotides from the 5'-end of the primer (shown in quotation marks in Table 3) was labeled with 6-carboxy fluorescein as described in Example 1.

TABLE 2

Various Universal tag lengths (CTCCX; X = 0-11 bp)*

| Reaction | Forward primer (SEQ ID NO:) | Universal Tag Length |
|---|---|---|
| 1 | 5'-c"t"ccggcccgccgagATGACGGGTAACGGGGAAT (8) | 15 mer |
| 2 | 5'-c"t"ccggcccgcATGACGGGTAACGGGGAAT (9) | 11 mer |
| 3 | 5'-c"t"ccggcATGACGGGTAACGGGGAAT (10) | 7 mer |
| 4 | 5'-c"t"ccgATGACGGGTAACGGGGAAT (11) | 5 mer |
| 5 | 5'-c"t"ccATGACGGGTAACGGGGAAT (12) | 4 mer |

*The reverse primer for all reactions was 5'-CCAATTACAAAACCAAAAAGTCC (SEQ ID NO: 13).
*Universal primer sequence shown in lowercase; sequence-specific primer shown in uppercase.
"T" includes 6-carboxy fluorescein.

The *C. parvum* 18S sequence was amplified using real-time PCR, and a melting curve obtained, as described in Example 1.

Figure 6A:
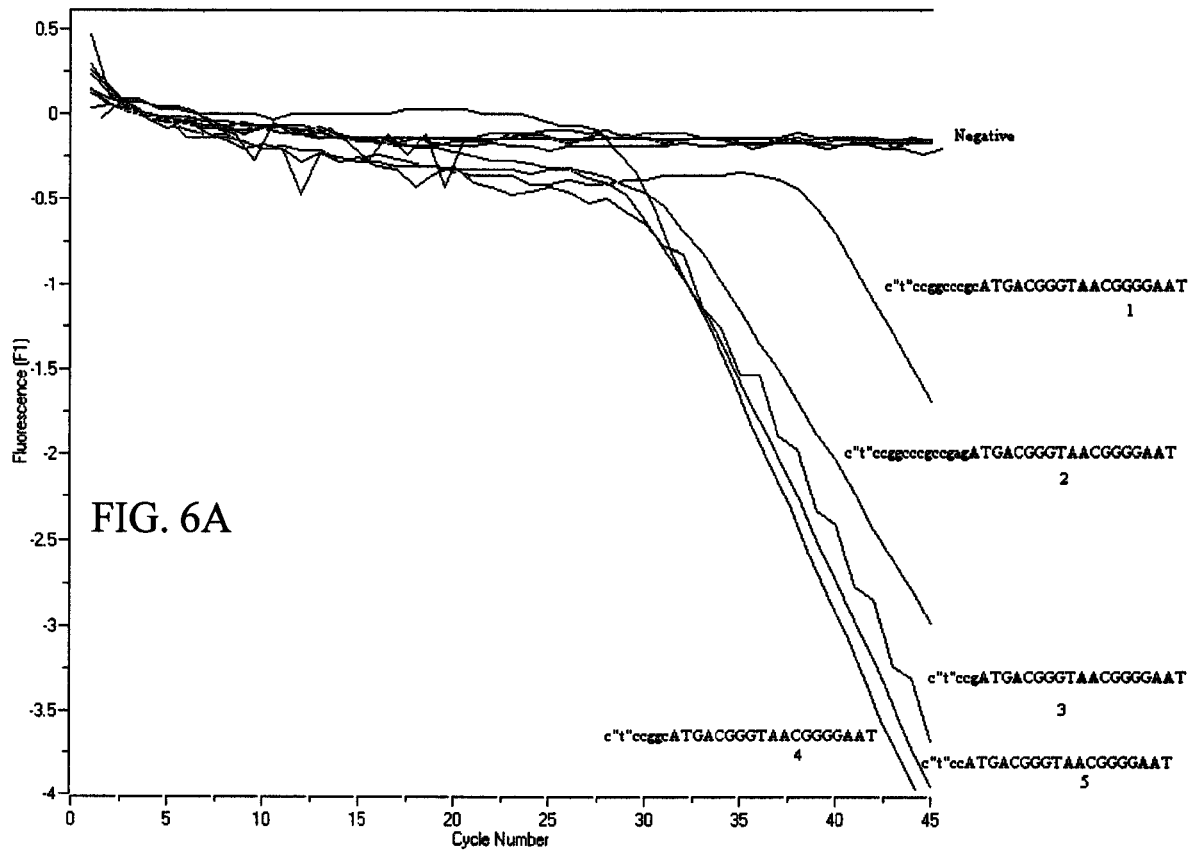
FIG. 6A is a graph showing fluorescence quenching curves obtained by real-time PCR amplification of a *Cryptosporidium parvum* sequence using 5'-CTCCX$_{(0-11)}$-3' (SEQ ID NO: 7) as exemplary universal tags as shown in the figure.
Figure 6B:
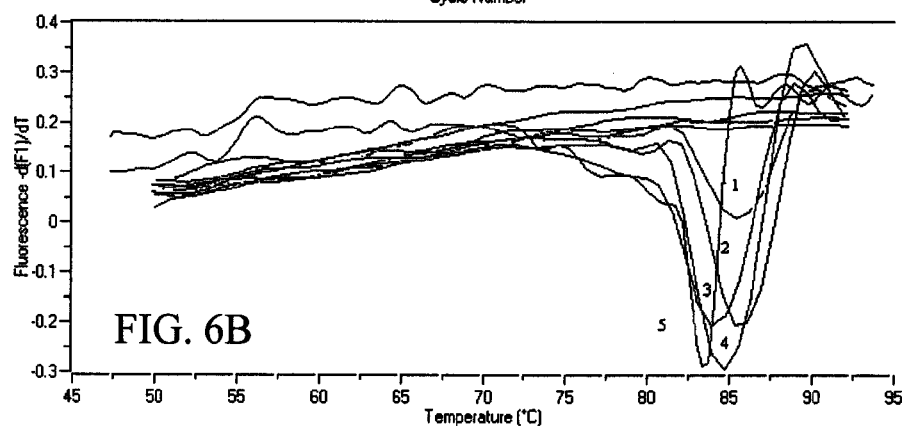
FIG. 6B is a graph showing the melting curve analysis using 5'-CTCCX$_{(0-11)}$-3' (SEQ ID NO: 7) as exemplary universal tags.

As shown in FIG. 6A, different universal tag lengths resulted in different rates of quenching; however all worked.

TABLE 3

| | Seven-mer UniFluor tag (CTCCXXX)* | |
|---|---|---|
| Microbe | Forward primer (SEQ ID NO:) | Reverse primer (SEQ ID NO:) |
| Adenovirus | c"t"ccggcGGACGCCTCGGAGTAC CTGAG (15) | ACIGTGGGGTTTCTGAACTT GTT (3) |
| Salmonella | c"t"ccggcGCCTTTCTCCATCGTCC TGA (16) | TGGTGTTATCTGCCTGACC (17) |
| Cryptosporidium | c"t"ccggcAT GAC GGG TAA CGG GGA AT(10) | CCAATTACAAAACCAAAAA GTCC (13) |
| Hepatitis E Virus | c"t"ccggcGGTGGTTTCTGGGGTG AC (26) | AGGGGTTGGTTGGATGAA (27) |

*Universal primer sequence shown in lowercase; sequence-specific primer shown in uppercase.
"T" includes 6-carboxy fluorescein.

The adenovirus hexon protein region sequence was amplified using real-time PCR using SEQ ID NOS: 15 and 3, the *S. typhimurium* fimA sequence was amplified using PCR using SEQ ID NOS: 16 and 17, and the *C. parvum* 18S sequence was amplified by PCR using SEQ ID NOS: 10 and 13, using the methods described in Example 1.

Hepatitis E Virus ORF3 region was amplified using RT-PCR with SEQ ID NOS: 26 and 27 as described in Example 3.

As shown in FIGS. 7A and 9A, fluorescence-quenching curves were obtained by real-time PCR for the detection of AdV40 and *S. typhimurium* using universal primers of 7-bp in length. The melting curve analysis of the product produced in these reactions is shown in FIG. 7B. Similar results were obtained for *C. parvum* (see FIGS. 6A and 7B).

Example 6

Use of Thermostable Restriction Enzyme to Cleave the Universal Fluorescent Primer This example describes methods that can be used to detect the presence of a nucleic acid molecule through increase in fluorescence.

In one example, the method includes amplification of a target nucleic acid sequence using a universal fluorescent primer CC"T"GG. The PCR reaction can be performed in the presence of the thermostable restriction enzyme BstNI that cleaves the fluorescent tag when double stranded DNA and the universal fluorescent sequence forms a cleavable substrate for thermostable endonuclease such as BstNI. The universal primer remains single-stranded in the absence of target nucleic acid molecule, and is not acted upon by BstNI. However, during target-dependent synthesis a complementary strand is synthesized and becomes nickable by the restriction endonuclease. The cleavage cuts the fluorescent-labeled primer, thereby separating it from the complimentary guanosine quencher. This leads to increase in fluorescence intensity.

In another example, the method includes amplification of a target nucleic acid sequence using a universal fluorescent primer CC"T"GG under isothermal conditions. For example, NASBA, 3 SR, TMA, and so on, can be performed using the universal tags disclosed herein by substituting one primer with a universal tag while the other primer contains the RNA polymerase promoter. The promoter sequence, located on the 5' end of the second primer, generates RNA copies complementary to the universal tag. This sequence will hybridize to the universal tag and RNA transcriptase will extend the universal tag extension product. However, during target-dependent synthesis a complementary strand is synthesized and becomes nickable by the restriction endonuclease. The cleavage cuts the fluorescent-labeled primer, thereby separating it from the complimentary guanosine quencher. This leads to increase in fluorescence intensity.

Example 7

Use of Universal Tags with an Array

This example describes methods that can be used to detect the presence of a nucleic acid molecule using the disclosed universal tags in combination with an array, such as a microarray.

In one example, the method includes amplification of a target nucleic acid sequence using a universal tag attached to the forward or reverse primer. The primer not containing a universal tag can include another label, such as a fluorophore, such as Cy3 or Cy5. For example, real-time PCR can be performed using a forward primer labeled with a universal tag using the methods disclosed herein, and a labeled reverse primer (for example labeled with Cy3 or Cy5). The resulting amplicons can be analyzed using the methods disclosed herein to determine if the sample analyzed is positive or negative for the target nucleic acid of interest.

The resulting PCR products (amplicons) from the positive reactions can be denatured at 100° C. for 2 minutes and chilled on ice immediately prior to hybridization to an array containing one or more nucleic acid sequence targets of interest. A particular example of such a microarray is a DNA chip. In one example, the amino group of the target nucleic acid molecule can be linked at its 5' end to the surface of the array. If the target nucleic acid sequence is present on the array, the amplicons previously generated (which contain at least one detectable label, such as 2 detectable labels) will hybridize to the target nucleic acid one the array. The resulting hybridization will produce an increase in signal due to the present of the detectable label on the amplicon. For example, if one of the primers included Cy3 or Cy5, the resulting Cy3 or Cy5 labeled product will produce an increase in fluorescence intensity, which can be detected and in some examples further quantitated.

Such a method can be used to confirm the positive or negative results obtained with amplification using a universal tag disclosed herein.

Example 8

Use of Universal Tags with Pyrosequencing

This example describes methods that can be used to sequence a nucleic acid molecule using the disclosed universal tags in combination with pyrosequencing.

In one example, the method includes amplification of a target nucleic acid sequence using a universal tag attached to the 5' end of a forward or reverse primer. The primer not containing a universal tag can include biotin at its 5' end. The labeled forward and reverse primers are used to amplify a target nucleic acid sequence, for example by using real-time PCR methods disclosed herein. The resulting amplicons can be analyzed using the methods disclosed herein to determine if the sample analyzed is positive or negative for the target nucleic acid of interest. The resulting amplicons would contain a detectable biotin label.

The biotin labeled amplicon is separated after denaturation and adhesion of the amplicons to streptavidin-coated magnetic beads. The separated strands are then sequenced using pyrosequencing with an appropriate sequencing primer, using methods known in the art (for a review of pyrosequencing see Franca et al., *Q. Rev. Biophys.* 35(2):169-200, 2002).

Example 9

Detection of a Nucleic Acid Molecule in a Subject

This example describes methods to determine if a particular nucleic acid molecule is present, for example present in a sample obtained from a subject.

In one example, the method includes amplification of a target nucleic acid sequence from a sample using a universal tag attached to the forward or reverse primer. In one example, the sample is obtained from a subject infected or suspected of being infected with a pathogen, such as a virus, bacterium, parasite, fungi, or combinations thereof. In this example, the target nucleic acid sequence can be a sequence specific to the pathogen of interest, or a nucleic acid molecule of the subject whose expression is altered (such as increased or decreased) in response to the infection, or combinations thereof.

In another example, the sample is obtained from a subject having or suspected of having a disease, such as cancer. In particular examples, the subject is being treated or has been treated for the disease, and the method is used to determine the subject's response to the treatment. In this example, the target nucleic acid sequence can be a nucleic acid molecule of the subject whose expression is altered (such as increased or decreased) due to the disease, a control sequence (such as a sequence that detects expression of a housekeeping gene), or combinations thereof. Housekeeping genes are known in the art (for example see Janssens et al., *Mol. Diagn.* 8(2):107-13, 2004), and can include porphobilinogen deaminase (PBGD); mitochondrial ATP synthase 6 (mATPsy6); and glyceraldehyde-3-phosphate dehydrogenase (GAPDH). Ideally, a housekeeping gene has expression levels that remain relatively constant in different experimental conditions.

The primer not containing a universal tag can include another label, such as a fluorophore, such as Cy3 or Cy5. For example, real-time PCR can be performed using a forward primer labeled with a universal tag using the methods disclosed herein, and an unlabeled or labeled reverse primer (for example labeled with Cy3 or Cy5). The resulting amplicons can be analyzed using the methods disclosed herein to determine if the sample analyzed is positive or negative for the target nucleic acid of interest. If desired, the amplicons can be further analyzed, for example using an array, to confirm the amplification results. In some examples, quantitation of the target nucleic acid is performed.

Example 10

Single-Labeled Probe that Includes Stem and Loop Structure Attached to Forward Primer In particular examples, a UniFluor probe does not include a quenching fluorophore. For example, a UniFluor probe can include a specific probe sequence that is held in a hairpin loop configuration by complimentary stem sequences on the 5' and 3' sides of the probe. The internal labeling with 6-carboxy fluorescein of a "T" that is the second nucleotide (5'-C"T"C-CGCCC; nucleotides 1-8 of SEQ ID NO: 29) from the 5'-end is quenched by a complimentary arm sequence of 3'-GAG-GCGGG (SEQ ID NO: 30) joined to the 3'-end of the loop. The probe is attached to the primer via a PCR blocker (X) in order to reduce or prevent the extension of the primer so that the probe can hybridize to its own strand upon extension of the primer. In a particular example, the blocker is a C3 or C5 spacer, such as the C3 spacer amidite. When the probe hybridizes within the same strand, the hairpin loop opens to an extent such that there is no more quenching due to the guanosine nucleotides on the complementary arm.

This example describes methods to amplify *C. parvum* sequences using the primers as follows. Although this example describes amplification and detection of *C. parvum* using this primer, the disclosed method and primers can be used to amplify any nucleic acid molecule of interest. The forward primer is attached with the exemplary probe at the 5' end, with the probe consisting of stem and loop sequences. The stem portion does not bind to a target sequence, such as 5'-c"t"ccgccCGCGCCTGCTGCCTTCCTTA-GATGggcggag(X)ATGACGGGTAACGGG GAAT-3' (SEQ ID NO: 29) and reverse primer SEQ ID NO: 13. During target-dependent synthesis the probe part hybridizes to its target only when the target site has been incorporated into the same molecule by extension of the tailed primer. The hybridization of the probe to its target separates the complementary guanosine quencher stem. This results in the emission of fluorescence.

Figure 11:
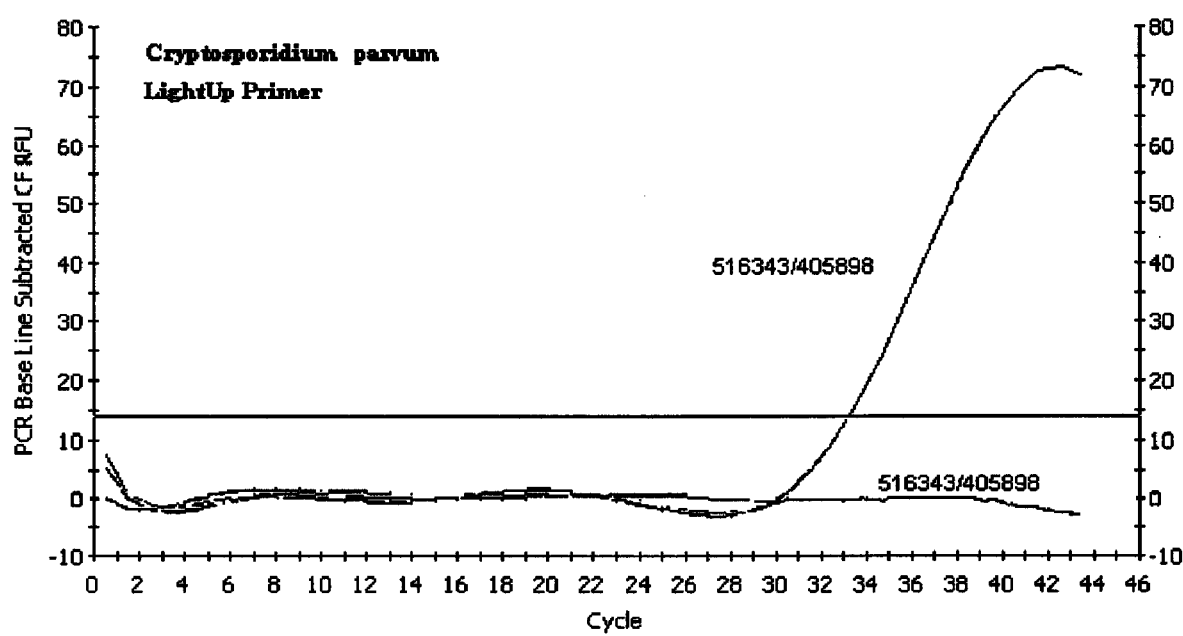
FIG. 11 is a graph showing the increase in fluorescence during amplification of *C. parvum* using SEQ ID NO: 29 and SEQ ID NO: 13.

This method was demonstrated in a real-time PCR assay using SEQ ID NOS: 29 and 13 using the methods described in Example 1. As shown in FIG. 11, the UniFluor probe results in fluorescence during amplification of the target sequence. However, in the negative samples no increase in signal was detected during amplification, thus demonstrating the specificity of the UniFluor probe.

The real-time PCR assay was performed using the QuantiTect™ Probe PCR kit (Qiagen, USA) and an iCycler iQ Real-Time PCR detection system (Bio-Rad laboratories, Hercules, Calif.). Amplification reactions contained 2 µL template DNA, 0.25 mM primers (SEQ ID NOS: 29 and 13), in a final reaction volume of 20 µL. The protocol took approximately 90 minutes to complete with the following PCR conditions: hot-start denaturation step at 95° C. for 15 minutes, followed by 45 cycles with a 95° C. denaturation for 10 seconds and 60° C. annealing for 60 seconds and collecting the fluorescence signal (F) at the end of this step (FIG. 11).

In another example, the method includes the use of a probe made of a stem and loop structure and hybridization of the probe to its complementary sequences during the amplification of the target nucleic acid sequence. The loop consists of a nucleic acid sequence that specifically hybridizes to a target complementary sequence. The stem portion of the probe is labeled internally with 6-carboxy fluorescein at "t" that is the second nucleotide from the 5'-end (c"t"ccgccCGCGCCT-GCTGCCTTCCTTAGATGggcggag; nucleotides 1-38 of SEQ ID NO: 29) and is quenched by complementary arm sequence of 5'GGCGGAG joined to the 3'-end of the loop. During target-dependent synthesis, the stem part of the probe separates and the loop part of the probe hybridizes to its specific complimentary strand. This functions as an oligonucleotide probe having a single fluorescent label.

In view of the many possible embodiments to which the principles of the disclosure can be applied, it should be recognized that the illustrated embodiments are only examples of the disclosure and should not be taken as limiting the scope of the disclosure. Rather, the scope of the disclosure is defined by the following claims. We therefore claim as our invention all that comes within the scope and spirit of these claims.

We claim:

1. A method of making a fluorescently-labeled sequence-specific primer, comprising:
   adding a universal nucleic acid sequence to a sequence-specific primer, thereby generating a fluorescently-labeled sequence-specific primer,
   wherein the universal nucleic acid sequence comprises
      a 5' end,
      a 3' end; and
      a fluorescently-labeled nucleotide flanked on each side by at least one nucleotide, wherein nucleotides complementary to the nucleotides flanking the fluorescently-labeled nucleotide quench a detectable signal from the label fluorophore when the fluorescently-labeled sequence-specific primer is hybridized with its complementary nucleic acid molecule and the complementary nucleic acid is synthesized,
   wherein the sequence-specific primer can hybridize to a target nucleic acid sequence,
   wherein the fluorophore can be quenched by the nucleotides complementary to the nucleotides flanking the fluorescently-labeled nucleotide, and
   wherein the universal nucleic acid sequence does not substantially hybridize to the target nucleic acid sequence recognized by the sequence-specific primer.

2. The method of claim 1, wherein the universal nucleic acid sequence comprises the sequence 5'-$X_2X_3X_4X_{5(n)}$-3', wherein $X_2$ and $X_4$ are "C", $X_3$ is any nucleotide, and $X_{5(n)}$ is any number of nucleotides.

3. The method of claim 2, wherein $X_3$ is "T".

4. The method of claim 2, wherein the $X_{5(n)}$ is C.

5. The method of claim 2, wherein the sequence 5'-$X_2X_3X_4X_{5(n)}$-3', comprises the sequence CTCC.

6. The method of claim 1, wherein the universal nucleic acid sequence comprises the sequence 5'-CTCS$X_{(n)}$-3' (SEQ ID NO: 20), wherein $X_{(n)}$ is any number of nucleotides, wherein S is G or C, and wherein T is the labeled nucleotide and is the second nucleotide from the 5'-end of the universal nucleic acid sequence.

7. The method of claim 6, wherein n comprises 3-50 nucleotides.

8. The method of claim 6, wherein n comprises 3-20 nucleotides.

9. The method claim 6, wherein n comprises 3-11 nucleotides.

10. The method of claim 6, wherein the universal nucleic acid sequence comprises the sequence 5'-CTCSXXX-3' (SEQ ID NO: 21), wherein X is any nucleotide, wherein S is G or C, and wherein T is the labeled nucleotide and is the second nucleotide from the 5'-end of the universal nucleic acid sequence.

11. The method of claim 6, wherein the universal nucleic acid sequence comprises the nucleic acid sequence shown in SEQ ID NO: 1, 6, 14, 18, 19, 21, or 22.

12. The method of claim 1, wherein the universal nucleic acid sequence is at least 4 nucleotides.

13. The method of claim 12, wherein the universal nucleic acid sequence is 4 to 25 nucleotides.

14. The method of claim 12, wherein the universal nucleic acid sequence is 4 to 15 nucleotides.

15. The method of claim 1, wherein the universal nucleic acid sequence comprises the sequence 5'-CTCSXXX$_{(n)}$-3' (SEQ ID NO: 22), wherein T is the labeled nucleotide and is the second nucleotide from the 5'-end of the universal nucleic acid sequence and n comprises 0-11 nucleotides.

16. The method of claim 1, wherein the labeled nucleotide is thymidine.

17. The method of claim 1, wherein a signal emitted by the fluorophore is decreased by guanosine in the complementary nucleic acid molecule.

18. The method of claim 1, wherein the fluorophore comprises 6-carboxyfluorescein (6-FAM); 5-carboxyfluorescein (5-FAM); boron dipyrromethene difluoride (BODIPY); N,N,N',N'-tetramethyl-6-carboxyrhodamine (TAMRA); acridine; stilbene; 6-carboxyfluorescein hexachloride (HEX); or derivatives thereof.

19. The method of claim 1, wherein a 5'-end of the sequence-specific primer is added to the 3'-end of the universal nucleic acid sequence.

20. The method of claim 1, wherein sequence-specific primer comprises at least nine nucleotides.

21. The method of claim 1, wherein the sequence-specific primer comprises a forward primer.

22. The method of claim 1, wherein the sequence-specific primer comprises a reverse primer.

23. A method of making a fluorescently-labeled sequence-specific primer, comprising:
   adding a fluorescently-labeled probe sequence to a sequence-specific primer, thereby generating a fluorescently-labeled sequence-specific primer,
   wherein the sequence-specific primer can hybridize to a target nucleic acid sequence,
   wherein the fluorescently-labeled probe sequence added to the sequence-specific primer comprises 5'-CTCSSSS$X_{(n)}$RRRRGAG-3' (SEQ ID NO:31),
   wherein $X_{(n)}$ is any number of nucleotides,
   wherein SSSS is complementary to RRRR, and each S is G or C,
   wherein T is a fluorescently-labeled nucleotide and is the second nucleotide from the end of the fluorescently-labeled probe sequence, wherein the CTCSSSS and RRRRGAG sequences of the fluorescently-labeled probe sequence are capable of hybridizing to each other, thereby quenching fluorescence from the fluorescently-labeled T, wherein the $X_{(n)}$ sequence is capable of hybridizing to a sequence that would be synthesized by extending the sequence-specific primer on the target nucleic acid sequence, thereby disrupting hybridization between the CTCSSSS and RRRGAG of the probe sequence, thereby increasing the fluorescent signal of the fluorescently-labeled T of the probe sequence.

24. The method of claim 23, wherein the fluorescently-labeled sequence-specific primer comprises 5'-CTCSSSS $X_{(n)}$RRRRGAGZ$X_{(n)}$-3' (SEQ ID NO:32), wherein $X_{(n)}$ at position 8 is any number of nucleotides and is capable of hybridizing to a sequence that would be synthesized by extending the sequence-specific primer on the target nucleic acid sequence, wherein $X_{(n)}$ at position 17 is any number of nucleotides and is the sequence-specific primer to which the fluorescently-labeled probe sequence was added to generate the fluorescently-labeled sequence-specific primer, wherein Z is a carbon spacer arm of at least 3 carbons.

25. The method of claim 24, wherein Z is a blocking moiety that can reduce or prevent synthesis of the complementary sequence of the CTCSSSSX$_{(n)}$RRRRGAG portion of SEQ ID NO:32.

* * * * *